US008815225B2

(12) United States Patent
Beumer et al.

(10) Patent No.: US 8,815,225 B2
(45) Date of Patent: Aug. 26, 2014

(54) HAIR CARE COMPOSITIONS

(75) Inventors: Raphael Beumer, Loerrach (DE);
Franciscus Derks, Heythuysen (NL);
Christine Mendrok,
Rheinfelden-Minseln (DE)

(73) Assignee: DSM IP Assets B.V., Heerlen (NL)

( * ) Notice: Subject to any disclaimer, the term of this patent is extended or adjusted under 35 U.S.C. 154(b) by 617 days.

(21) Appl. No.: 12/281,032

(22) PCT Filed: Feb. 23, 2007

(86) PCT No.: PCT/EP2007/001575
§ 371 (c)(1),
(2), (4) Date: Aug. 28, 2008

(87) PCT Pub. No.: WO2007/098888
PCT Pub. Date: Sep. 7, 2007

(65) Prior Publication Data
US 2009/0068136 A1 Mar. 12, 2009

(30) Foreign Application Priority Data
Mar. 3, 2006 (EP) .................................... 06004344

(51) Int. Cl.
C08G 69/44 (2006.01)
A61K 8/88 (2006.01)
A61K 8/49 (2006.01)
A61Q 5/00 (2006.01)
A61Q 5/06 (2006.01)
A61Q 5/02 (2006.01)
A61Q 5/04 (2006.01)
A61Q 5/12 (2006.01)

(52) U.S. Cl.
CPC ............. *C08G 69/44* (2013.01); *A61K 2800/54* (2013.01); *A61K 8/88* (2013.01); *A61Q 5/06* (2013.01); *A61Q 5/02* (2013.01); *A61Q 5/12* (2013.01)
USPC .................................................... 424/70.17

(58) Field of Classification Search
CPC ....... A61K 2800/54; A61K 8/88; A61Q 5/02; A61Q 5/06; A61Q 5/12; C08G 69/44
USPC ..................................................... 424/70.17
See application file for complete search history.

(56) References Cited

U.S. PATENT DOCUMENTS

| 3,479,310 | A | * | 11/1969 | Bayer et al. ................ 524/591 |
| 3,905,929 | A | * | 9/1975 | Noll ............................. 524/839 |
| 3,961,042 | A | * | 6/1976 | Green et al. ................. 424/78.32 |
| 4,013,787 | A | * | 3/1977 | Varlerberghe et al. ...... 424/70.17 |
| 4,238,378 | A | * | 12/1980 | Markusch et al. ............ 524/591 |
| 4,515,658 | A | * | 5/1985 | Fong ........................... 162/168.4 |
| 5,030,443 | A |   | 7/1991 | Varco et al. |
| 5,447,539 | A | * | 9/1995 | Kelly et al. ...................... 8/485 |
| 5,726,137 | A |   | 3/1998 | Patel et al. |
| 6,635,262 | B2 | * | 10/2003 | Jourdan et al. ................ 424/400 |
| 6,638,321 | B1 | * | 10/2003 | Genet et al. ....................... 8/407 |
| 6,730,771 | B2 |   | 5/2004 | Van Benthem et al. |
| 6,875,245 | B2 |   | 4/2005 | Pavlin |
| 6,881,400 | B2 |   | 4/2005 | Collin |
| 7,459,167 | B1 | * | 12/2008 | Sengupta et al. ............. 424/405 |
| 2002/0019509 | A1 |   | 2/2002 | Van Benthem et al. |
| 2002/0034486 | A1 | * | 3/2002 | Midha et al. ................ 424/70.2 |
| 2002/0187170 | A1 |   | 12/2002 | Pavlin |
| 2002/0189030 | A1 |   | 12/2002 | Collin |
| 2003/0057158 | A1 | * | 3/2003 | Klomp .......................... 210/698 |
| 2003/0236387 | A1 |   | 12/2003 | Pavlin |
| 2004/0054037 | A1 | * | 3/2004 | Abbeele van den et al. ... 524/47 |
| 2004/0228886 | A1 | * | 11/2004 | Ding et al. .................... 424/401 |
| 2005/0244353 | A1 | * | 11/2005 | Lendlein et al. ............. 424/70.1 |
| 2007/0202071 | A1 | * | 8/2007 | Morvan et al. .............. 424/70.17 |
| 2008/0038215 | A1 | * | 2/2008 | Derici et al. ................ 424/70.11 |
| 2008/0081025 | A1 | * | 4/2008 | Poschalko et al. .............. 424/60 |
| 2008/0317696 | A1 | * | 12/2008 | Derici et al. ................ 424/70.12 |
| 2011/0165107 | A1 |   | 7/2011 | Derks et al. |
| 2011/0182843 | A1 |   | 7/2011 | Derks et al. |

FOREIGN PATENT DOCUMENTS

| EP | 0 121 091 | | 10/1984 | |
| WO | 00/58388 | | 10/2000 | |
| WO | WO 00/58388 | * | 10/2000 | ............. C08G 69/44 |
| WO | WO 2006/013200 | | 2/2006 | |
| WO | WO 2007/144189 | | 2/2007 | |
| WO | WO 2007/098888 | | 9/2007 | |
| WO | WO 2007/100392 A2 | | 9/2007 | |

OTHER PUBLICATIONS

Polymer Factory (Polyester Amide—Hybrane®, [Downloaded Nov. 16, 2013] [Retrieved from internet <URL: http://www.polymerfactory.com/hyperbranched-polymers/polyester-amide-hybrane >]), 7 pages.*
"Amides" (Jack DeRuiter, Principles of Drug Action 1 (2005), Amides and Related Functional Groups, [Downloaded Nov. 16, 2013] [Retrieved from internet <URL: http://www.auburn.edu/~deruija/pda1_amides.pdf >]), 16 pages.*
"Amines" (Jack DeRuiter, Principles of Drug Action 1 (2005), Amines and Quaternary Ammonium Compounds, [Downloaded Nov. 17, 2013] [Retrieved from internet <URL: http://www.auburn.edu/~deruija/pda1_amines.pdf >]), 21 pages.*
Jack DeRuiter, professor at Auburn's Pharmacy School [Downloaded Nov. 16, 2013] [Retrieved from internet <URL:http://pharmacy.auburn.edu/personnel.aspx?dept=14&query=deruija .], 1 page.*

(Continued)

*Primary Examiner* — Jason Sims
*Assistant Examiner* — Miriam A Levin
(74) *Attorney, Agent, or Firm* — Nixon & Vanderhye P.C.

(57) ABSTRACT

The invention relates to hair care compositions comprising an effective amount of a condensation polymer having at least one, optionally quarternized or protonated, dialkylamide endgroup connected through the polymer backbone to a unit derived from an alkylamide, the connection comprising at least one ester linkage.

27 Claims, No Drawings

(56) References Cited

OTHER PUBLICATIONS van Benthem et al. (Synthesis and Characterization of Bis(2-hydroxypropyl)amide-Based Hyperbranched Polyesteramides, Macromolecules (2001), 34: 3559-3566), 8 pages.*

Froehling, Development of DSM's Hybrane® Hyperbranched Polyesteramides, Journal of Polymer Science, Part A: Polymer Chemistry, (2004) 42:3110-3115 (6 pages).*

International Search Report for PCT/EP2007/001575, mailed Jul. 16, 2007.

Written Opinion of the International Searching Authority for PCT/EP2007/001575, mailed Jul. 16, 2007.

International Preliminary Report on Patentability issued in PCT/EP2009/057646 (WIPO, Dec. 21, 2010), 6 pages.

International Search Report for PCT/EP2009/057646, mailed Sep. 30, 2009.

International Search Report for PCT/EP2009/057647, mailed Sep. 23, 2009.

* cited by examiner

HAIR CARE COMPOSITIONS

This application is the U.S. national phase of International Application No. PCT/EP2007/001575, filed 23 Feb. 2007, which designated the U.S. and claims priority to Europe Application No. 06004344.5 filed 3 Mar. 2006, the entire contents of each of which are hereby incorporated by reference.

The invention relates to hair care compositions comprising an effective amount of a condensation polymer having at least one, optionally quarternized or protonated, dialkylamide end-group connected through the polymer backbone to a unit derived from an alkylamide, the connection comprising at least one ester linkage.

In hair care products the use of polymers is gaining more and more importance, for example to improve the rheological behaviour of the product or to enhance the adhesion of other ingredients to the hair. Thus, there is a growing need for polymers suitable for use in hair care compositions fulfilling the manifold requirements posed on such polymers in regard of availability, easy handling and/or cost/performance.

In hair care preparation for example film forming polymers are used e.g. as conditioning agent in order to improve the combability, the shine and the visible appearance of the hair as well as to give the hair antistatic properties.

Commercially available polymers for hair care such as hair styling or conditioning polymers are e.g. copolymers of vinyl acetate and crotonic acid, copolymers of methyl vinyl ether and maleic anhydride, copolymers of acrylic acid or methacrylic acid with other monomers, polyurethanes, N-vinylpyrrolidone and silicone polymers.

The aim of the invention was to provide easily available, cost efficient hair care compositions comprising an effective amount of a condensation polymer having an, optionally quarternized, dialkylamide end-group connected through the polymer backbone to a unit derived from an alkylamide, the connection comprising at least one ester linkage. The hair care composition should fulfil a variety of requirements such as exhibiting low stickiness, lack of powdering or flaking, preferably being clear, transparent and glossy. Additionally, hair care compositions should offer excellent performance e.g. in regard of good film formation, good holding power, high level of style retention, prolonged curl retention, improved combability, and should be easily removed upon washing the hair with shampoo or soap.

Polymers suitable for the incorporation into hair care compositions should exhibit a excellent heat stability, very good solubility, compatibility with cosmetic bases, pH stability in the range of 4 to 9, processability into a variety of products, compatibility with other ingredients and with the packaging materials and should be free of color and be of neutral or pleasant odor and have a low volatility.

It has now surprisingly been found that condensation polymers having at least one, optionally quarternized, dialkylamide end-group connected through the polymer backbone to a unit derived from an alkylamide, the connection comprising at least one ester linkage (in the following referred to as condensation polymer) are especially suitable for the preparation of hair care compositions.

It has also be found that they can be used as conditioning agents, strengthening agents, film forming agents, surfactants, anti-static agents, moisturizers, emulsifiers or hair styling agents in hair care compositions.

Thus, the invention relates to hair care compositions comprising an effective amount of a condensation polymer having at least one, optionally quarternized or protonated, dialkylamide end-group connected through the polymer backbone to a unit derived from an alkylamide, the connection comprising at least one ester linkage.

In one embodiment the present invention relates to hair care compositions comprising a condensation polymer having at least one special end-group according to formula (I) connected to the polymer characterized in that the polymer contains at least two groups according to formula (I)

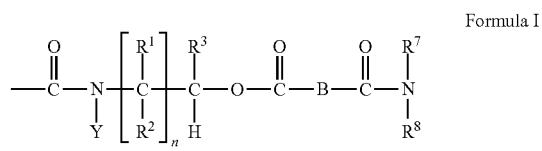

Formula I wherein
Y is

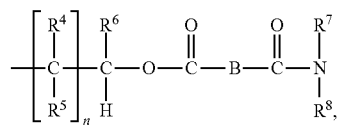

a hydrogen atom, a linear, branched or cyclic $(C_1-C_{20})$ alkyl group or a $(C_6-C_{10})$ aryl group;
B is a $(C_6-C_{24})$ aryldiradical or a $(C_2-C_{24})$ alkyldiradical;
$R^1$, $R^2$, $R^3$, $R^4$, $R^5$ and $R^6$ are, independently of each other, hydrogen atoms, $(C_6-C_{10})$ aryl groups or $(C_1-C_8)$ alkyl groups;
$R^7$ and $R^8$ are, independently of each other, optionally heteroatom substituted $(C_6-C_{10})$ aryl groups or optionally heteroatom substituted $(C_1-C_{28})$ alkyl groups or
$R^7$ and $R^8$ together with the nitrogen atom to which they are attached form a 5 or 6 membered ring wherein optionally one or several C-atoms are replaced by —NH, —N—$(C_1-C_{20})$ alkyl, —N-aryl, —O— or —S—;
and n is an integer of 1 to 4. Preferably, n is 1.

According to another embodiment, the hair care compositions comprise a polymer according to formula (II):

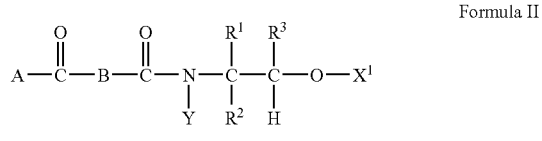

Formula II in which:
Y is

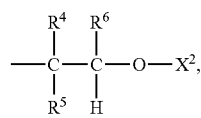

a hydrogen atom, a $(C_1-C_{20})$ alkyl group or a $(C_6-C_{10})$ aryl group;
A is

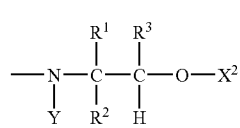

or OH;
B is a $(C_6-C_{24})$ aryl diradical or a $(C_2-C_{24})$ alkyl diradical;

$X^1$ is

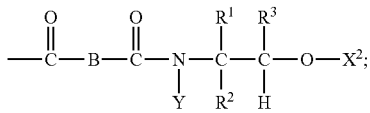

$X^2$ is

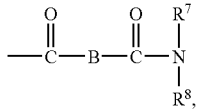

a hydrogen atom or $X^1$;

$R^1$, $R^2$, $R^3$, $R^4$, $R^5$ and $R^6$ are, independently of each other, hydrogen atoms,
  ($C_6$-$C_{10}$) aryl groups or ($C_1$-$C_8$) alkyl groups or —$CH_2$—$OX^2$;

$R^7$ and $R^8$ are, independently of each other, optionally heteroatom substituted
  ($C_6$-$C_{10}$) aryl groups or optionally heteroatom substituted ($C_1$-$C_{28}$) alkyl groups or $R^7$ and $R^8$ together with the nitrogen atom to which they are attached form a 5 or 6 membered ring wherein optionally one or several C-atoms are replaced by —NH—, —N—($C_1$-$C_{20}$) alkyl, —N-aryl, —O— or —S—.

Preferably $R^1$, $R^2$ are both hydrogen atoms.

In another embodiment the invention relates to hair care composition characterized in that the condensation polymer is either linear or branched.

According to a further embodiment of the invention, the hair care compositions comprise a condensation polymer characterized in that the number of the dialkyl amide end-groups is equal or greater than 3.

Furthermore, the invention relates to hair care compositions comprising a condensation polymer characterized in that the polymer is represented by formula (III):

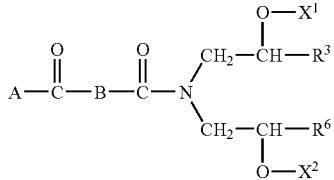

Formula III in which

A is

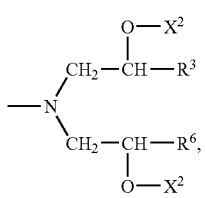

or OH;

B is a ($C_6$-$C_{24}$) aryldiradical or a ($C_2$-$C_{24}$) alkyldiradical;

$X^1$ is

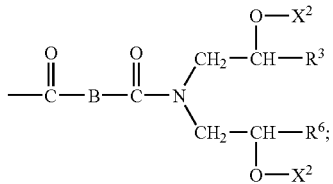

$X^2$ is

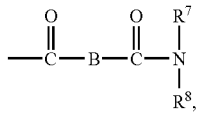

a hydrogen atom or $X^1$;

$R^3$ and $R^6$ are, independently of each other, hydrogen atoms, ($C_6$-$C_{10}$) aryl groups or ($C_1$-$C_8$) alkyl groups or —$CH_2$—$OX^2$;

$R^7$ and $R^8$ are, independently of each other, optionally heteroatom substituted ($C_6$-$C_{10}$) aryl groups or optionally heteroatom substituted ($C_1$-$C_{28}$) alkyl groups or $R^7$ and $R^8$ together with the nitrogen atom to which they are attached form a 5 or 6 membered ring wherein optionally one or several C-atoms are replaced by —NH—, —N—($C_1$-$C_{20}$) alkyl, —N-aryl, —O— or —S—.

In all above embodiments, preferably, $R^3$ and $R^6$ are linear or branched ($C_1$-$C_4$) alkyl groups, more preferably a methyl- or ethyl group.

In all above embodiments, preferably, $R^7$ and $R^8$ are optionally heteroatom substituted ($C_1$-$C_{20}$) alkyl groups.

More preferably, $R^7$ and $R^8$ are linear $C_2$-, $C_3$- or $C_6$-alkyl groups wherein optionally one or several C-atoms are substituted by nitrogen, oxygen or sulfur.

$R^7$ and $R^8$ may be substituted with a group selected from the group of alcohol, ether, ester, cyanide, carbonate, urethane, urea, amide, imide, amine, imine or imidazole.

Suitable choices for $R^7$ and $R^8$ are di(m)ethylaminoethyl, di(m)ethylaminopropyl, di(m)ethylaminohexyl, 2-(benz)imidazole-ethyl, diphenylphosphino-ethyl and/or diallylamine groups.

$R^7$ and $R^8$ together with the nitrogen atom to which they are attached may form an optionally substituted 5 or 6 membered ring wherein, optionally, one or several C-atoms are substituted by —NH—, —N—($C_1$-$C_{20}$) alkyl, —N-aryl, —O— or —S—. Such optionally substituted 5 or 6 membered rings are e.g. morpholine, piperidine, pyrrolidine, piperazine or N-methylpiperazine, and derivatives thereof.

Most preferred, $R^7$ and $R^8$ are selected from N,N-dimethylaminopropyl, and/or groups derived from N-methylpiperazine.

In all formulas in this application in which R-groups are present, the R groups may together or with neighbouring carbon atoms form part of a cycloalkyl group.

Depending on the starting monomers chosen, B, $R^1$, $R^2$, $R^3$, $R^4$, $R^5$, $R^6$, $R^7$ and $R^8$ in the molecule or mixture of molecules can be selected to be the same or different.

B is optionally substituted, preferably with a ($C_1$-$C_{26}$) alkyl group. Preferably, the alkyl group is chosen from the group of methyl, octenyl, nonenyl, decenyl, undecenyl or dodecenyl.

Suitable choices for B are (alkyl-)-1,2-ethylene, where the alkyl is defined as above, (methyl-)-1,2-ethylidene, 1,3-propylene, (methyl-)-1,2-cyclohexyl, (methyl-)-1,2-phenylene, 1,3-phenylene, 1,4-phenylene, 2,3-norbornyl, 2,3-norbornen-5-yl, tetrahydro-1,2-phenylene or (methyl-)-1,2 cyclohex-4-enyl radical.

Preferably, the weight average molecular mass of the condensation polymer incorporated into the hair care compositions according to the invention is between 600 g/mol and 50,000 g/mol, more preferably between 800 g/mol and 25,000 g/mol.

Preferably, the number average molecular mass is between 500 g/mol and 15,000 g/mol, more preferably between 700 g/mol and 4,000 g/mol.

The average molecular weight can be determined by methods known to a person skilled in the art. For example, the number average molecular weight of a polymer can be determined by vapor pressure osmometry, end-group titration and/or colligative properties. The weight average molecular weight can e.g. be determined by light scattering, small angle neutron scattering (SANS), X-ray scattering, and sedimentation velocity.

Preferably, the average number dialkylamide end-groups per molecule is between 2 and 250, more preferably between 3 and 50.

The condensation polymer comprised in hair care compositions according to the invention can be linear or branched. The linear polymer generally comprises amide and ester units alternating along a chain as follows:

wherein a diamide (A-A) unit is coupled with alternating ester (E) and amide (A) units.

A branched condensation polymer comprised in hair care compositions according to the invention generally comprises amide and ester units alternating along the main and side chains as follows:

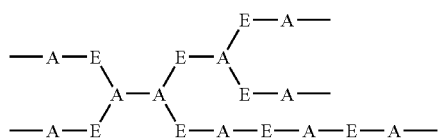

wherein a diamide (A-A) is coupled with alternating ester (E) and amide (A) units.

Preferably, in the branched polymer a (β)-hydroxyalkylamide group is present, which can be both present as a bis-(β)-hydroxyalkylamide end-group, such as

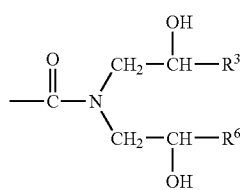

or as a pendant side chain group, such as

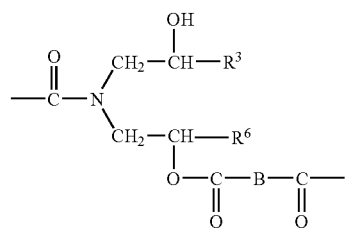

Preferably, the molar amount of amide units in the chain is higher than the molar amount of ester units.

In all above embodiments, optionally one or several nitrogen atoms of the condensation polymer may be present in quaternized forms or may be protonated. This means that nitrogen atoms present in the condensation polymer such as e.g. amino groups in the NHet group are protonated with hydrogen or are quaternized with linear, branched or cyclic $(C_1-C_8)$ alkyl groups, unsaturated $(C_1-C_8)$ alkyl groups, aryl groups, (meth-)acrylic groups or mixtures thereof. Furthermore, one or several nitrogen atoms of the condensation polymer may be converted into a betaine group. The quaternization, respectively the protonation leads to a positively charged condensation polymer. The counter ion may result from the quaternization, respectively protonation agent such as $Cl^-$, $Br^-$, $SO_4^{2-}$, $PO_4^{3-}$, $MeSO_4^-$, $EtSO_4^-$, without being limited thereto.

Preferably, the nitrogen atoms are quaternized with methyl and/or ethyl groups.

The non-quaternized or protonated amine functionalized condensation polymer comprised in hair care composition according to the invention can be obtained through polycondensation of a mono- and/or bis-hydroxyalkylamide of a dicarboxylic acid in the presence of a mono-dialkyl amide of a dicarboxylic acid as disclosed in EP 1 171 510 (p. 7ff, in particular page 7, line 21 to page 19, line 14) which is included herein by reference.

The optionally one or several nitrogen atoms of the condensation polymer which are present in quaternized forms or are protonated may be prepared by reaction of the nitrogen atoms of the non-quaternized condensation polymer with customary quaternizing or protonation agents according to standard procedures as e.g. described in Jerry March, 'Advanced organic chemistry, $4^{th}$ edition, Wiley-Interscience.

Suitable quaternization reagents are e.g. alkyl or aryl halides such as Me iodide, Me chloride, phenyl iodide, allyl chloride, vinyl chloride; sulfates such as dimethylsulfate, diethylsulfate; glycidyl ethers and esters such as allyl glycidyl ether and glycidyl methacrylate without being limited thereto. Suitable quaternization agents to obtain the betaine group are chloro acetic acid and (meth-)acrylic acid. The quaternization procedure can take place with or without a solvent. Suitable solvents are water or an organic solvent, such as e.g. acetonitril. The quaternized condensation polymer can be used as solution in the respective solvent or the solvent can be evaporated to yield a dried condensation polymer.

Suitable protonation agents are e.g. inorganic acids such as HCl; $H_3PO_4$; $H_2SO_4$; the protonation procedure can take place with or without a solvent. Suitable solvents are water or an organic solvent, such as e.g. acetonitril. The protonated condensation polymer can be used as solution in the respective solvent or the solvent can be evaporated to yield a dried condensation polymer.

Dependent on the desired degree of the quaternization, respectively protonation, the amount of quaternization or protonation agent to nitrogen atoms has to be adjusted accordingly.

The preferred degree of quaternization, respectively protonation, of the nitrogen atoms of the condensation polymer is between 20 and 100%, more preferred between 50 and 100%, most preferred 80 and 100%.

The term "effective amount" means generally at least a concentration of 0.01% by weight based on the total formulation. Preferably, a concentration of 0.01-20 wt. %, most preferred of 0.05-10 wt. % is used.

In a further embodiment the invention relates to hair care preparations comprising a condensation polymer as outlined above and additional cosmetic or dermatological adjuvants and/or additives.

In a preferred embodiment the hair care preparations according to the invention are characterized in that the hair care compositions are shampoo preparations or hair styling preparations The invention furthermore relates to the use of a condensation polymer as described above in hair care preparations as conditioning agent, strengthening agent, film forming agent, surfactant, anti-static agent, moisturizer, emulsifier or hair styling agent.

Additionally, the invention relates to a method of treating hair in which a hair care composition comprising the condensation polymer as described above is applied to the hair.

Compounds of the above Formula I, Formula II and Formula III characterized in that $R^7$ and $R^8$ together with the nitrogen atom to which they are attached form a 5 or 6 membered ring wherein optionally one or several C-atoms are replaced by —NH, —N—$(C_1$-$C_{20})$alkyl, —N-aryl, —O— or —S— and wherein one or several nitrogen atoms are present in quaternized forms or are protonated are novel and, as such, also form part of the invention.

Preferred are condensation polymers of the above Formula I, Formula II and Formula III characterized in that $R^7$ and $R^8$ together with the nitrogen to which they are attached form a N-methylpiperazine group wherein one or several nitrogen atoms are present in quaternized forms or are protonated.

The hair care compositions according to the invention comprise additional cosmetic or dermatological adjuvants and/or additives (cosmetic carrier) which are preferable selected from 1.) Water
2.) Water soluble organic solvents, preferably $C_1$-$C_4$-Alkanols
3.) Oils, fatty substances, waxes
4.) Various esters different to 3) of $C_6$-$C_{30}$ monocarbonic acids with one, two, or three valent alcohols
5.) Saturated acyclic and cyclic hydrocarbons
6.) Fatty acids
7.) Fatty alcohols
8.) Silicone oils
and mixtures thereof.

The hair care compositions according to the invention can contain further adjuvants and additives such as preservatives/antioxidants, fatty substances/oils, water, organic solvents, silicones, thickeners, softeners, emulsifiers, screening agents, antifoaming agents, moisturizers, fragrances, surfactants, fillers, sequestering agents, anionic-, cationic-, nonionic- or amphoteric polymers or mixtures thereof, propellants, acidifying or basifying agents, dyes, colorants, pigments or nanopigments, light stabilizers, insect repellents, antibacterial agents, preservatives or any other ingredients usually formulated into hair care compositions. The necessary amounts of the adjuvants and additives can, based on the desired product, easily be chosen by a skilled artisan in this field and will be illustrated in the examples, without being limited hereto.

Light Screening Agents

Light screening agents are advantageously selected from UV-A, UV-B, UV-C and/or broadband filters. Examples of UV-B or broad spectrum screening agents, i.e. substances having absorption maximums between about 290 and 340 nm may be organic or inorganic compounds. Organic UV-B or broadband screening agents are e.g. acrylates such as 2-ethylhexyl 2-cyano-3,3-diphenylacrylate (octocrylene, PARSOL® 340), ethyl 2-cyano-3,3-diphenylacrylate and the like; camphor derivatives such as 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid and the like; Cinnamate derivatives such as ethylhexyl methoxycinnamate (PARSOL® MCX), ethoxyethyl methoxycinnamate, diethanolamine methoxycinnamate (PARSOL® Hydro), isoamyl methoxycinnamate and the like as well as cinnamic acid derivatives bond to siloxanes; p-aminobenzoic acid derivatives, such as p-aminobenzoic acid, 2-ethylhexyl p-dimethylaminobenzoate, N-oxypropylenated ethyl p-aminobenzoate, glyceryl p-aminobenzoate; benzophenones such as benzophenone-3, benzophenone-4, 2,2',4,4'-tetrahydroxybenzophenone, 2,2'-dihydroxy-4,4'-dimethoxybenzophenone and the like; esters of benzalmalonic acid such as di-(2-ethylhexyl) 4-methoxybenzalmalonate; esters of 2-(4-ethoxy-anilinomethylene)propandioic acid such as 2-(4-ethoxy anilinomethylene) propandioic acid diethyl ester as described in the European Patent Publication EP 0895 776; organosiloxane compounds containing benzmalonate groups as described in the European Patent Publications EP 0358584 B1, EP 0538431 B1 and EP 0709080 A1 such as polysilicone-15 (PARSOL® SLX); drometrizole trisiloxane (Mexoryl XL); imidazole derivatives such as e.g. 2-phenyl benzimidazole sulfonic acid and its salts (PARSOL® HS). Salts of 2-phenyl benzimidazole sulfonic acid are e.g. alkali salts such as sodium- or potassium salts, ammonium salts, morpholine salts, salts of primary, sec. and tert. amines like monoethanol amine salts, diethanol amine salts and the like; salicylate derivatives such as isopropylbenzyl salicylate, benzyl salicylate, butyl salicylate, ethylhexyl salicylate (PARSOL® EHS, NEO Heliopan OS), isooctyl salicylate or homomethyl salicylate (homosalate, PARSOL® HMS, NEO Heliopan OS) and the like; triazine derivatives such as ethylhexyl triazone (Uvinul T-150), diethylhexyl butamido triazone (Uvasorb HEB). Encapsulated UV-filters such as encapsulated ethylhexyl methoxycinnamate (Eusolex UV-pearls) or microcapsules loaded with UV-filters as e.g. disclosed in EP 1471995 and the like. Inorganic compounds are pigments such as microparticulated $TiO_2$, ZnO and the like. The term "microparticulated" refers to a particle size from about 5 nm to about 200 nm, particularly from about 15 nm to about 100 nm. The $TiO_2$ particles may also be coated by metal oxides such as e.g. aluminum or zirconium oxides or by organic coatings such as e.g. polyols, methicone, aluminum stearate, alkyl silane. Such coatings are well known in the art.

Examples of broad spectrum or UV A screening agents i.e. substances having absorption maximums between about 320 and 400 nm may be organic or inorganic compounds e.g. dibenzoylmethane derivatives such as 4-tert. butyl-4'-methoxydibenzoyl-methane (PARSOL® 1789), dimethoxydibenzoylmethane, isopropyldibenzoylmethane and the like; benzotriazole derivatives such as 2,2'-methylene-bis-(6-(2H-benzotriazol-2-yl)-4-(1,1,3,3,-tetramethylbutyl)-phenol (TINOSORB M) and the like; bis-ethylhexyloxyphenol methoxyphenyl triazine (Tinosorb S) and the like; phenylene-1,4-bis-benzimidazolsulfonic acids or salts such as 2,2-(1,4-phenylene)bis-(1H-benzimidazol-4,6-disulfonic acid) (Neoheliopan AP); amino substituted hydroxybenzophenones such as 2-(4-Diethylamino-2-hydroxy-benzoyl)-benzoic acid hexylester (Uvinul A plus) as described in the European Patent Publication EP 1046391; Ionic UV-A filters as described in the International Patent Publication WO2005080341 A1. Pigments such as microparticulated ZnO or $TiO_2$ and the like. The term "microparticulated" refers to a particle size from about 5 nm to about 200 nm, particularly from about 15 nm to about 100 nm. The particles may also be coated by other metal oxides such as e.g. aluminum or zirconium oxides or by organic coatings such as e.g. polyols, methicone, aluminum stearate, alkyl silane. Such coatings are well known in the art.

As dibenzoylmethane derivatives have limited photostability it may be desirable to photostabilize these UV-A screening agents. Thus, the term "conventional UV-A screening agent" also refers to dibenzoylmethane derivatives such as e.g. PARSOL® 1789 stabilized by, e.g. 3,3-Diphenylacrylate derivatives as described in the European Patent Publications EP 0 514 491 B1 and EP 0 780 119 A1; Benzylidene camphor derivatives as described in the U.S. Pat. No. 5,605,680; Organosiloxanes containing benzmalonate groups as described in the European Patent Publications EP 0358584 B1, EP 0538431 B1 and EP 0709080 A1.

Antioxidants

Based on the invention all known antioxidants usually formulated into hair care compositions can be used. Especially preferred are antioxidants chosen from the group consisting of amino acids (e.g. glycine, histidine, tyrosine, tryptophan) and their derivatives, imidazole (e.g. urocanic acid) and derivatives, peptides such as D,L-carnosine, D-carnosine, L-carnosine and derivatives (e.g. anserine), carotenoids, carotenes (e.g. α-carotene, p-carotene, lycopene) and derivatives, chlorogenic acid and derivatives, lipoic acid and derivatives (e.g. dihydrolipoic acid), aurothioglucose, propylthiouracil and other thiols (e.g. thioredoxine, glutathione, cysteine, cystine, cystamine and its glycosyl-, N-acetyl-, methyl-, ethyl-, propyl-, amyl-, butyl- and lauryl-, palmitoyl-; oleyl-, γ-linoleyl-, cholesteryl- and glycerylester) and the salts thereof, dilaurylthiodipropionate, distearylthiodipropionate, thiodipropionic acid and its derivatives (ester, ether, peptides, lipids, nucleotides, nucleosides and salts) as well as sulfoximine compounds (such as buthioninsulfoximine, homocysteinesulfoximine, buthioninsulfone, penta-, hexa-, heptathioninsulfoximine) in very low compatible doses (e.g. pmol bis μmol/kg), additionally (metal)-chelators (such as α-hydroxyfatty acids, palmic-, phytinic acid, lactoferrin), β-hydroxyacids (such as citric acid, lactic acid, malic acid), huminic acid, gallic acid, gallic extracts, bilirubin, biliverdin, EDTA, EGTA and its derivatives, unsaturated fatty acids and their derivatives (such as γ-linoleic acid, linolic acid, oleic acid), folic acid and its derivatives, ubiquinone and ubiquinol and their derivatives, vitamin C and derivatives (such as ascorbylpalmitate and ascorbyltetraisopalmitate, Mg-ascorbylphosphate, Na-ascorbylphosphate, ascorbyl-acetate), tocopherol and derivates (such as vitamin-E-acetate), mixtures of nat. vitamin E, vitamin A and derivatives (vitamin-A-palmitate and -acetate) as well as coniferylbenzoate, rutinic acid and derivatives, α-glycosylrutin, ferulic acid, furfurylideneglucitol, carnosine, butylhydroxytoluene, butylhydroxyanisole, trihydroxybutyrophenone, urea and its derivatives, mannose and derivatives, zinc and derivatives (e.g. ZnO, $ZnSO_4$), selen and derivatives (e.g. selenomethionin), stilbenes and derivatives (such as stilbenoxide, trans-stilbenoxide) and suitable derivatives (salts, esters, ethers, sugars, nucleotides, nucleosides, peptides and lipids) of the named active ingredients. One or more preservatives/antioxidants may be present in an amount of at least 0.01 wt. % of the total weight of the composition. Preferably about 0.01 wt. % to about 10 wt. % of the total weight of the composition of the present invention is present. Most preferred, one or more preservatives/antioxidants are present in an amount about 0.1 wt. % to about 1 wt. %.

Surface Active Ingredients

Typically hair care compositions also contain surface active ingredients like emulsifiers, solubilizers and the like. An emulsifier enables two or more immiscible components to be combined homogeneously. Moreover, the emulsifier acts to stabilize the composition. Emulsifiers that may be used in the present invention in order to form O/W, W/O, O/W/O or W/O/W emulsions/microemulsions include sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polyglyceryl-4 oleate/PEG-8 propylene glycol cocoate, oleamide DEA, TEA myristate, TEA stearate, magnesium stearate, sodium stearate, potassium laurate, potassium ricinoleate, sodium cocoate, sodium tallowate, potassium castorate, sodium oleate, and mixtures thereof. Further exemplary emulsifiers are phosphate esters and the salts thereof such as cetyl phosphate (Amphisol® A), diethanolamine cetyl phosphate (Amphisol®), potassium cetyl phosphate (Amphisol® K), sodium glyceryl oleate phosphate, hydrogenated vegetable glycerides phosphate and mixtures thereof. Furthermore, one or more synthetic polymers may be used as an emulsifier. For example, PVP eicosene copolymer, acrylates/$C_{10-30}$ alkyl acrylate crosspolymer, acrylates/steareth-20 methacrylate copolymer, PEG-22/dodecyl glycol copolymer, PEG-45/dodecyl glycol copolymer, and mixtures thereof. Further exemplary emulsifiers are fatty alcohols, e.g. cetearyl alcohol (Lanette O, Cognis Coopearation), cetyl alcohol (Lanette 16, Cognis Cooperation), stearyl alcohol (Lanette 18, Cognis Coopearation), Laneth-5 (Polychol 5, Croda Chemicals), furthermore sucrose and glucose derivatives, e.g. sucrose distearate (Crodesta F-10, Croda Chemicals), Methyl glucose isostearate (Isolan IS, Degussa Care Chemicals), furthermore ethoxylated carboxylic acids or polyethyleneglycol esters and polyethyleneglycol ethers, e.g. steareth-2 (Brij 72, Uniqema), steareth-21 (Brij 721, Uniqema), ceteareth-25 (Cremophor A25, BASF Cooperation), PEG-40 hydrogenated castor oil (Cremophor RH-40, BASF Cooperation), PEG-7 hydrogenated castor oil (Cremophor WO7, BASF Cooperation), PEG-30 Dipolyhydroxystearate (Arlacel P 135, Uniqema), furthermore glyceryl esters and polyglyceryl esters, e.g. polyglyceryl-3-diisostearate (Hostacerin TGI, Clariant Cooperation), polyglyceryl-2 dipolyhydroxystearate (Dehymuls PGPH, Cognis Cooperation), polyglyceryl-3 methylglucose distearate (Tego Care 450, Degussa Care Chemicals). The preferred emulsifiers are cetyl phosphate (Amphisol® A), diethanolamine cetyl phosphate (Amphisol®), potassium cetyl phosphate (Amphisol® K), PVP Eicosene copolymer, acrylates/$C_{10-30}$-alkyl acrylate crosspolymer, PEG-20 sorbitan isostearate, sorbitan isostearate, and mixtures thereof. The one or more emulsifiers are present in a total amount of at least 0.01 wt. % of the total weight of the composition. Preferably about 0.01 wt. % to about 20 wt. % of the total weight of the composition of the present invention is used. Most preferred, about 0.1 wt. % to about 10 wt. % of emulsifiers are used.

Typically hair care compositions also contain anionic, neutral, amphoteric or cationic tensides.

Exemplary anionic tensides comprise alkylsulfate, alkylethersulfate, alkylsulfonate, alkylarylsulfonate, alkylsuccinate, alkylsulfosuccinate, N-alkoylsarkosinate, acyltaurate, acylisethionate, alkylphosphate, alkyletherphosphate, alkylethercarboxylate, alpha-olefinsulfonate, especially the alkali-und earth alkali salts, e.g. sodium, potassium, magnesium, calcium, as well as ammonium- and triethanol amine-salts.

The alkylethersulfate, alkyletherphosphate and alkylethercarboxylate may comprise between 1 to 10 ethylenoxide or propylenoxide units, preferably 1 to 3 ethylenoxide-units per molecule.

Suitable are e.g. sodium laurylsulfate, ammonium lauryl sulfate, sodium laurylethersulfate, ammonium laurylethersulfate, sodium lauroylsarkonisate, sodiumoleylsuccinate, ammonium laurylsulfosuccinate, sodium dodecylbenzolsulfonate, triethanolamidodecylbenzolsulfonate.

Suitable amphoteric tensides are e.g. alkylbetaine, alkylamidopropylbetaine, alkylsulfobetaine, alkylglycinate, alkylcarboxyglycinate, alkylamphoacetate or propionate, alkylamphodiacetate or dipropionate such as cocodimethylsulfopropylbetain, laurylbetain, cocamidopropylbetain or sodium cocamphopropionate.

Examples of non ionic tensides are e.g. reaction products of aliphatic alcohols or alkylphenols with 6 to 20 C-Atoms of a linear or branched alkyl chain with ethylenoxide and/or propylenoxide. The amount of alkylenoxide is about 6 to 60 mole to one mol alcohol. Furthermore alkylaminoxide, mono- or dialkylalkanolamide, fatty esters of polyethylen glycols, alkylpolyglycosides or sorbitanether ester are suitable for the incorporation of hair care compositions according to the invention.

Furthermore, the hair care compositions may contain the usual cationic tensides such as quaternised ammonium compounds e.g. cetyltrimethylammoniumchlorid or bromide (INCI: cetrimoniumchloride or bromide), hydroxyethylcetyldimonium phosphate (INCI: Quaternium-44), Luviquat® Mono LS (INCI: Cocotrimoniummethosulfate), poly (oxy-1,2-Ethandiyl), (Octadecylnitrilio) tri-2,1-Ethandiyl) tris-(hydroxy)-phosphate (INCI Quaternium-52).

For special effects typical conditioning agents may be combined with the condensation polymers within the hair car preparations such as the previously mentioned cationic polymers named polyquaternium (INCI), especially copolymers of vinylpyrrolidone/N-vinylimidazolium salts (Luviquat® FC, Luviquat® HM, Luviquat® MS, Luviquat® Ultracare), copolymers of N-vinylpyrrolidone/dimethylaminoethylmethacrylate quaternised with diethylsulfate (Luviquat® PQ 11), copolymers of N-cationic cellulose derivatives (Polyquaternium-4 and -10), acrylamidcopolymers (Polyquaternium-7). Furthermore protein hydrolysates may be used as well as conditioning agents on silicone basis such as polyarylsiloxane, polyarylalkylsiloxane, polyethersiloxane or silicone resins. Other suitable silicone compounds are dimethicondopolyole (CTFA) and amino functionalised silicone derivatives such as amodimethicone (CTFA). Furthermore cationic guar derivatives such as guarhydroxypropyltrimoniumchloride (INCI) may be used.

The one or more anionic, neutral, amphoteric or cationic tensides are present in a total amount of at least 0.01 wt. % of the total weight of the composition. Preferably about 0.01 wt. % to about 20 wt. % of the total weight of the composition of the present invention is used. Most preferred, about 0.1 wt. % to about 10 wt. % of one or more tensides are used.

Oil and Fatty Components

The lipid phase can advantageously be chosen from mineral oils and mineral waxes; oils such as triglycerides of caprinic acid and/or caprylic acid or castor oil; oils or waxes and other natural or synthetic oils, in an preferred embodiment esters of fatty acids with alcohols e.g. isopropanol, propyleneglycol, glycerin or esters of fatty alcohols with carbonic acids or fatty acids; alkylbenzoates; and/or silicone oils.

Exemplary fatty substances which can be incorporated in the oil phase of the emulsion, microemulsion, oleo gel, hydrodispersion or lipodispersion of the present invention are advantageously chosen from esters of saturated and/or unsaturated, linear or branched alkyl carboxylic acids with 3 to 30 carbon atoms, and saturated and/or unsaturated, linear and/or branched alcohols with 3 to 30 carbon atoms as well as esters of aromatic carboxylic acids and of saturated and/or unsaturated, linear or branched alcohols of 3-30 carbon atoms. Such esters can advantageously be selected from octylpalmitate, octylcocoate, octylisostearate, octyldodecylmyristate, cetearylisononanoate, isopropylmyristate, isopropylpalmitate, isopropylstearate, isopropyloleate, n-butylstearate, n-hexyllaurate, n-decyloleate, isooctylstearate, isononylstearate, isononylisononanoate, 2-ethyl hexylpalmitate, 2-ethylhexyllaurate, 2-hexyldecylstearate, 2-octyldodecylpalmitate, stearylheptanoate, oleyloleate, oleylerucate, erucyloleate, erucylerucate, tridecylstearate, tridecyltrimellitate, as well as synthetic, half-synthetic or natural mixtures of such esters e.g. jojoba oil.

Other fatty components suitable for hair care compositions of the present invention include polar oils such as lecithins and fatty acid triglycerides, namely triglycerol esters of saturated and/or unsaturated, straight or branched carboxylic acid with 8 to 24 carbon atoms, preferably of 12 to 18 carbon-atoms whereas the fatty acid triglycerides are preferably chosen from synthetic, half synthetic or natural oils (e.g. cocoglyceride, olive oil, sun flower oil, soybean oil, peanut oil, rape seed oil, sweet almond oil, palm oil, coconut oil, castor oil, hydrogenated castor oil, wheat oil, grape seed oil, macadamia nut oil and others); apolar oils such as linear and/or branched hydrocarbons and waxes e.g. mineral oils, vaseline (petrolatum); paraffins, squalane and squalene, polyolefins, hydrogenated polyisobutenes and isohexadecanes, favored polyolefins are polydecenes; dialkyl ethers such as dicaprylylether; linear or cyclic silicone oils such as preferably cyclomethicone (octamethylcyclotetrasiloxane; cetyldimethicone, hexamethylcyclotrisiloxane, polydimethylsiloxane, poly(methylphenylsiloxane) and mixtures thereof.

Other fatty components which can advantageously be incorporated in hair care compositions of the present invention are isoeikosane; neopentylglycoldiheptanoate; propyleneglycoldicaprylate/dicaprate; caprylic/capric/diglycerylsuccinate; butyleneglycol caprylat/caprat; $C_{12-13}$-alkyllactate; di-$C_{12-13}$-alkyltartrate; triisostearin; dipentaerythrityl hexacaprylat/hexacaprate; propyleneglycolmonoisostearate; tricaprylin; dimethylisosorbid. Especially beneficial is the use of mixtures $C_{12-15}$-alkylbenzoate and 2-ethylhexylisostearate, mixtures $C_{12-15}$-alkylbenzoate and isotridecylisononanoate as well as mixtures of $C_{12-15}$-alkylbenzoate, 2-ethylhexylisostearate and isotridecyl-isononanoate.

The oily phase of the formulation of the present invention can also contain natural vegetable or animal waxes such as bee wax, china wax, bumblebee wax and other waxes of insects as well as shea butter and cocoa butter.

Silicone Oils

Suitable silicone oils are e.g. dimethylpolysiloxane, diethylpolysiloxane, diphenylpolysiloxane, cyclic siloxanes, poly(methylphenylsiloxanes) as well as amino-, fatty acid-, alcohol-, polyether-, epoxy-, fluor-, glycoside-, and/or alkyl modified silicone compounds which are liquid or solid at room temperature and mixtures thereof. The number average molecular weight of the dimethicones and poly(methylphenylsiloxanes) is preferably in the range of 100 to 150000 g/mol. Preferred cyclic siloxanes comprise 4- to 8-membered rings which are for example commercially available as cyclomethicones.

An oil or fatty component is present in an amount of about 1 wt. % to about 50 wt. % of the total weight of the product. The preferred amount of an oil or fatty component is about 2 wt. % to about 25 wt. %, and most preferably about 3 wt. % to about 20 wt. %.

Moisturizing Agents

A moisturizing agent may be incorporated into a product of the present invention to maintain hydration or rehydrate the hair. Moisturizers that prevent water from evaporating by providing a protective coating are called emollients. Additionally an emollient provides a softening or soothing effect on the hair surface. Preferred emollients include mineral oils, lanolin, petrolatum, capric/caprylic triglyceraldehydes, cholesterol, silicones such as dimethicone, cyclomethicone, almond oil, jojoba oil, avocado oil, castor oil, sesame oil, sunflower oil, coconut oil and grape seed oil, cocoa butter, olive oil, aloe extracts, fatty acids such as oleic and stearic, fatty alcohols such as cetyl and hexadecyl (ENJAY), diisopropyl adipate, hydroxybenzoate esters, benzoic acid esters of $C_{9-15}$-alcohols, isononyl iso-nonanoate, ethers such as polyoxypropylene butyl ethers and polyoxypropylene cetyl ethers, and $C_{12-15}$-alkyl benzoates, and mixtures thereof. The most preferred emollients are hydroxybenzoate esters, aloe vera, $C_{12-15}$-alkyl benzoates, and mixtures thereof. An emollient is present in an amount of about 1 wt. % to about 50 wt. % of the total weight of the product. The preferred amount of emollient is about 2 wt. % to about 25 wt. %, and most preferably about 3 wt. % to about 15 wt. %.

Moisturizers that bind water, thereby retaining it on the hair surface are called humectants. Examples of humectants which can be incorporated into a product of the present invention are glycerine, propylene glycol, polypropylene glycol, polyethylene glycol, lactic acid, sodium lactate, pyrrolidone carboxylic acid, urea, phospholipids, collagen, elastin, ceramides, lecithin sorbitol, PEG-4, and mixtures thereof. Additional suitable moisturizers are polymeric moisturizers of the family of water soluble and/or swellable/and/or with water gelating polysaccharides such as hyaluronic acid, chitosan and/or a fucose rich polysaccharide which is e.g. available as Fucogel®1000 (CAS-Nr. 178463-23-5) by SOLABIA S. One or more humectants are optionally present at about 0.5 wt. % to about 8 wt. % in a product of the present invention, preferably about 1 wt. % to about 5 wt. %.

The aqueous phase of the products of the present invention can contain the usual cosmetic additives such as alcohols, especially lower alcohols, preferably ethanol and/or isopropanol, low diols or ethylene glycol monoethyl- or monobutylether, propylene glycol monomethyl- or -monoethyl- or -monobutylether, diethylene glycol monomethyl- or monoethylether and analogue products, polymers, foam stabilizers; electrolytes and especially one or more thickeners.

Thickeners

Thickeners that may be used in formulations of the present invention to assist in making the consistency of a product suitable include carbomer, siliciumdioxide, magnesium and/or aluminum silicates, lipid thickeners, e.g. cetyl alcohol, cetyl palmitate (Cutina CP, Cognis Cooperation), glyceryl myristate (Estol 3650, Uniqema), microcrystalline wax (A&E Connock), myristyl alcohol (Lanette 14, Cognis Cooperation), myristyl lactate (Crodamol ML, Croda Chemicals), beeswax (A&E Connock), stearic acid (Lipo Chemicals), stearyl alcohol (Lanette 18, Cognis Cooperation), polysaccharides and their derivatives such as xanthan gum (Keltrol, CP Kelco), hydroxypropyl cellulose (Klucel, Hercules Incorporated), Hydroxyethylcellulose (Tylose H, Clariant Corporation), polyacrylamides, selfemulsifying polyacrylamide, e.g. Salcare SC 91, Salcare SC 96 (Ciba Specialty Chemicals), Sepigel 305 (Seppic), acrylate crosspolymers, preferably a carbomer, such as Carbopolee of type 980, 981, 1382, 2984, 5984, ETD 2001, ETD 2050, Ultrez 10, Ultrez 21 (Noveon Inc.), alone or mixtures thereof. Thickeners can be present in an amount of about 0.01 wt. % to about 8 wt. % in the product of the present invention, preferably, 0.05 wt. % to about 5 wt. %.

Neutralizing Agents

Examples of neutralizing agents which may be included in the product of the present invention to neutralize components such as e.g. an emulsifier or a foam builder/stabilizer include but are not limited to alkali hydroxides such as a sodium and potassium hydroxide; organic bases such as diethanolamine (DEA), triethanolamine (TEA), aminomethyl propanol, and mixtures thereof; amino acids such as arginine and lysine and any combination of any foregoing. The neutralizing agent can be present in an amount of about 0.01 wt. % to about 8 wt. % in the product of the present invention, preferably, 1 wt. % to about 5 wt. %.

Electrolytes

The addition of electrolytes into the product of the present invention may be necessary to change the behavior of a hydrophobic emulsifier. Thus, the emulsions/microemulsions of this invention may contain preferably electrolytes of one or several salts including anions such as chloride, sulfate, carbonate, borate and aluminate, without being limited thereto. Other suitable electrolytes can be on the basis of organic anions such as, but not limited to, lactate, acetate, benzoate, propionate, tartrate and citrate. As cations preferably ammonium, alkylammonium, alkali- or alkaline earth metals, magnesium-, iron- or zinc-ions are selected. Especially preferred salts are potassium and sodium chloride, magnesium sulfate, zinc sulfate and mixtures thereof. Electrolytes can be present in an amount of about 0.01 wt. % to about 8 wt. % in the product of the present invention.

Light Stabilizers

The addition of further light stabilizers may be desirable. Such light stabilizers are e.g. known as sterically hindered amine light stabilizer (HALS) which can be of monomeric or polymeric nature. They are for example selected from the group consisting of N,N'-bisformyl-N,N'-bis-(2,2,6,6-tetramethyl-4-piperidinyl)-hexamethylenediamine (Uvinul 4050H), bis-(2,2,6,6-tetramethyl-4-piperidyl)sebacate (Uvinul 4077H), bis-(1,2,2,6,6-pentamethyl-4-piperidyl)sebacate+methyl-(1,2,2,6,6-pentamethyl-4-piperidyl)sebacate=(Uvinul 4092H), bis-(2,2,6,6-tetramethylpiperidin-4-yl) sebacate, bis-(2,2,6,6-tetramethylpiperidin-4-yl) succinate, bis-(1,2,2,6,6-pentamethylpiperidin-4-yl) sebacate, n-butyl-3,5-di-tert-butyl-4-hydroxybenzyl-malonic acid bis-(1,2,2,6,6-pentamethylpiperidyl) ester, the condensate of 1-hydroxyethyl-2,2,6,6-tetramethyl-4-hydroxypiperidine and succinic acid, the condensate of N,N'-bis-(2,2,6,6-tetramethyl-4-piperidyl)hexamethylenediamine and 4-tert-octylamino-2,6-dichloro-1,3,5-s-triazine, tris-(2,2,6,6-tetramethyl-4-piperidyl)nitrilotriacetate, tetrakis(2,2,6,6-tetra-methyl-4-piperidyl)-1,2,3,4-butanetetranoate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis-(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, the condensate of N,N-bis-(2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetra-methylpiperidyl)-1,3,5-triazine and 1,2-bis(3-aminopropylamino) ethane, the condensate of 2-chloro-4,6-di(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]-decane-2,4-dione, 3-dodecyl-1-(2,2,6,6-tetramethyl-4-piperidyl)pyrrolidin-2,5-dione, 3-dodecyl-1-(1,2,2,6,6-pentamethyl-14-piperidyl)-pyrrolidine-2,5-dione, a mixture of 4-hexadecyloxy- and 4-stearyloxy-2,2,6,6-tetramethylpiperidine, the condensate of N,N'-bis-(2,2,6,6-tetramethyl-4-piperidyl)hexamethylenediamine and 4-cyclohexylamino-2,6-dichloro-1,3,5-triazine, the condensate of 1,2-bis-(3-aminopropylamino) ethane and 2,4,6-trichloro-1,3,5-triazine and 4-butylamino-2,2,6,6-tetramethylpiperidine (CAS reg. No. [136504-96-6]); (2,2,6,6-tetramethyl-4-piperidyl)-n-dodecylsuccinimide, (1,2,2,6,6-pentamethyl-4-piperidyl)-n-dodecylsuccinimide, 2-undecyl-7,7,9,9-tetramethyl-1-oxa-3,8-diaza-4-oxo-spiro[4,5]decane, the reaction product of 7,7,9,9-tetramethyl-2-cycloundecyl-1-oxa-3,8-diaza-4-oxospiro[4,5]decane and epichlorohydrin without being limited thereto.

Insect Repellents

Examples of insect repellents which can be used in hair care compositions according to the invention are for example N,N-diethyl-m-toluamide, 1,2-pentanediol or insect repellent 3535.

Anti-Dandruff Agents

Examples of anti-dandruff agents which may be used are cimbazole, octopirox and zinc pyrithione. Customary film formers include, for example, chitosan, microcrystalline chitosan, quaternized chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Preservatives

Examples of preservatives include Methyl-, Ethyl-, Propyl-, Butylparabens, Benzalkonium chloride, 2-Bromo-2-nitro-propane-1,3-diol, Dehydroacetic acid, Diazolidinyl Urea, 2-Dichlorobenzyl alcohol, DMDM hydantoin, Formaldehyde solution, Methyldibromoglutaronitrile, Phenoxyethanol, Sodium Hydroxymethylglycinate, Imidazolidinyl Urea, Triclosan and further substance classes listed in the following reference: K. F. De Polo-A short textbook of cosmetology, Chapter 7, Table 7-2, 7-3, 7-4 and 7-5, p 210-219.

Bacteria-Inhibiting Agents

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido) hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorizing agent of interest is the terpene alcohol farnesol (3,7,11-tri-methyl-2,6,10-dodecatrien-1-ol), which is present in lime blossom oil. Glycerolmonolaurate has also proved to be a bacteriostatic agent. The amount of the additional bacteria-inhibiting agents present is usually from 0.1 to 2 wt. %, based on the solids content of the preparations.

Polymers

The compositions according to the invention may comprise additional polymers which are different from the condensation polymer in order to establish the desired properties. For this purpose all anionic-, cationic-, amphoteric- or neutral polymers may be used.

Examples for anionic polymers are homo- and copolymers of acrylic acid or methacrylic acid and the salts thereof; copolymers of acrylic acid and acryl amide and the salts thereof; sodium salts of polyhydroxy carbonic acids, water soluble or water dispersable polyester; polyurethanes such as Luviset Pur® of BASF and polyureas. Especially suitable are copolymers of t-butyl acrylate, ethylacrylate, methyl acrylic acid (e.g. Luvimer® 100P); copolymers of ethylacrylate and methacrylic acid (e.g. Luviflex® Soft); copolymers of N-tert.-butyl-acryl amide, ethylacrylate and acrylic acid (Ultrahold®, strong); copolymers of vinylacetate, crotonic acid and eventually other vinylic esters (e.g. Luviset® grades); copolymers of maleic acid anhydride; eventually with alcohols reacted anionic polysiloxanes e.g. carboxy functionalized, t-butylacrylate, methacrylic acid (Luviskol® VBM); copolymers of acrylic acid and methacrylic acid with hydrophobic monomers such as $C_4$-$C_{30}$-alkylester of methacrylic acid, $C_4$-$C_{30}$-alkylvinylester, $C_4$-$C_{30}$-alkylvinylether and hyaluronic acid. Examples of anionic polymers are also vinylacetate/crotonic acid copolymers (Resyn® by National Starch or Gafset® by GAF); vinylpyrrolidone/vinylacrylate copolymers (e.g. Luviflex® by BASF). Other suitable polymers are vinylpyrrolidone/acrylate terpolymer and sodiumsulfonate containing polyamides or sodiumsulfonate containing polyesters.

Additional polymers which can be used in combination with the condensation polymers comprises Balance® CR (National Starch; Acrylate Copolymer), Balance® 0/55 (National Starch; Acrylate Copolymer), Balances® 47 (National Starch; Octylacrylamide/Acrylate/Butylaminoethylmethacrylate-Copolymer), Aquaflex® FX 64 (ISP; Isobutylene/Ethylmaleimide/Hydroxyethylmaleimide-Copolymer), Aquaflex® SF-40 (ISP/National Starch; VP/vinylcaprolactam/DMAPA Acrylate Copolymer), Allianz® LT-120 (ISP/Rohm & Haas; Acrylate/C1-2 succinate/hydroxyacrylate copolymer), Aquarez® HS (Eastman; Polyester-1), Diaformer® Z-400 (Clariant; Methacryloylethylbetain/Methacrylate-Copolymer), Diaformer® Z-711 (Clariant; Methacryloylethyl N-oxid/Methacrylate-Copolymer), Diaformer® Z-712 (Clariant; Methacryloylethyl N-oxide/Methacrylate-Copolymer), Omnirez® 2000 (IS; Monoethylester from Poly(Methylvinylether/Maleic Acid in Ethanol), Amphomer® HC (National Starch; Acrylate/Octylacrylamide-Copolymer), Amphomer® 28-4910 (National Starch; Octyl-acrylamide/Acrylate/Butylaminoethylmethacrylate-Copolymer), Advantage® HC 37 (ISP; Terpolymer of vinyl-caprolactam/N-vinylpyrrolidon/dimethylaminoethyl-methacrylate), Advantage® LC55 und LC80 or LC A und LC E, Advantage® Plus (ISP; VA/butylmaleate/isobornylacrylate copolymer), Aculyne®258 (Rohm & Haas; Acrylate/Hydroxyesteracrylate-Copolymer), Luviset® P.U.R. (BASF, Polyurethane-1), Luviflex® Silk (BASF), Eastman® AQ 48 (Eastman), Styleze® CC-10 (ISP; VP/DMAPA Acrylates Copolymer), Styleze® 2000 (ISP; VP/Acrylates/Lauryl Methacrylate Copolymer), DynamX (National Starch; Polyurethane-14 AMP-Acrylates Copolymer), Resyn XP (National Starch; Acrylates/Octylacrylamide Copolymer), Fixomer A-30 (Ondeo Nalco; poly-methacrylic acid (and) acrylamidomethyl propanesulfonic acid), Fixate G-100 (Noveon; AMP-Acrylates/Allyl Methacrylate Copolymer).

Examples of cationic polymers are Polyquaternium (INCI), e.g. copolymers of vinylpyrrolidon/N-vinylimidazolium salts (Luviquat® FC, Luviquat® HM, Luviquat® MS, Luviquat® Ultracare), copolymers of N-vinylpyrrolidon/dimethylaminoethylmethacrylate, quaternized with diethylsulfate (Luviquat® PQ 11, INCI: Polyquaternium-11), copolymers of N-vinylcaprolactam/N-vinyl-pyrrolidon/N-vinylimidazolium salts (Luviquat® Hold; INCI: Polyquaternium-46); cationic derivatives of cellulose (Polyquaternium-4 and -10), acrylamidocopolymers (Polyquaternium-7), chitosan, cationic starch derivatives (INCI: starch hydroxypropyltrimonium chloride, corn starch modified), cationic guar derivates (INCI: hydroxypropyl guar hydroxypropyltrimonium chloride), cationic sun flower seed derivatives (INCI: sun flower seed amidopropyl hydroxyethyldimonium chloride), copolymers of acrylic acid, acrylamide and methacrylamidopropyltrimoniumchlorid (INCI: Polyquaternium-53), Polyquaternium-32, Polyquaternium-28 without being limited thereto. Suitable cationic quaternized polymers are furthermore Merquat® (polymers on the basis of dimethyldiallyl ammoniumchlorid), Gafquat® (quaternary polymers formed by reacting polyvinylpyrrolidone with quaternary ammonium compounds); Polymer JR (hydroxyethylcellulose with cationic groups), and cationic polymers on plant basis such as guar polymers, commercially available as Jaguar® grades of Rhodia.

Examples of neutral polymers are polyvinylpyrrolidone, copolymers of N-vinylpyrrolidone and vinylacetate and/or vinylpropionate, polysiloxane, polyvinylcaprolactam and other copolymers of N-vinylpyrrolidone, copolymers of N-vinylpyrrolidone and alkylacrylate or methacrylate monomers with $C_1$-$C_{18}$-alkyl chains, copolymers of polyvinylalcohol and polyalkylenglycole such as Kollicoats® IR (BASF) or copolymers of other vinyl monomers to polyalkylenglycole, polysiloxane, polyvinylcaprolactam and copolymers with N-vinylpyrrolidone, polyethylenimine and the salts thereof, polyvinylamine and the salts thereof, cellulose derivatives, chitosan, polyasparaginic acid salts and derivatives thereof, polyethylenimine and the salts thereof, polyvinylamine and the salts thereof such as Luviflex® Swing (partly hydrolysed copolymerisat of polyvinylacetate and polyethylenglycol by BASF).

Suitable polymers are also non-ionic, water soluble respectively water dispersible polymers or oligomers such as polyvinylcaprolactam, e.g. Luviskol® Plus (BASF), or polyvinylpyrrolidon and copolymers with e.g. vinylesters such as vinylacetate e.g. Luviskol® VA 37 (BASF); polyamide e.g. on the basis of itaconic acid and aliphatic diamines as e.g. described in DE-A-43 33 23.

Examples of amphoteric or zwitterionic polymers are octylacrylamide/methyl methacrylate/tert-butylaminoethyl methacrylate/2-hydroxypropyl methacrylate copolymers e.g. obtainable under the names Amphomer® (Delft National) and zwitterionic polymers as disclosed, for example, in German Patent Applications DE 39 29 973, DE 21 50 557, DE 28 17 369 and DE 37 08 451. Preferred zwitterionic polymers are acrylamidopropyltrimethylammonium chloride/acrylic acid or methacrylic acid copolymers and their alkali metal and ammonium salts. Other suitable polymers are methacroylethylbetaine/methacrylate copolymers, which are obtainable commercially under the name Amersette® (AMERCHOL) and copolymers of hydroxyethyl methacrylate, methyl methacrylate, N,N-dimethylaminoethyl methacrylate and acrylic acid (Jordapon®);

Additional suitable polymers are nonionic, siloxane-containing, water-soluble or -dispersible polymers, e.g. polyether siloxanes, such as Tegopren® (Goldschmidt) or Belsil® (Wacker).

Scents and Fragrances

The hair care compositions according to the invention may contain scents and fragrances comprising at least one, preferably numerous odorant ingredients of natural and/or synthetic origin. The range of the natural odorants includes, in addition to readily volatile, also moderately and only slightly volatile components. The synthetic odorants embrace representatives from practically all classes of odorant substances.

The following list comprises examples of known odorants which may be stabilized with the stabilizing composition according to the invention without being limited thereto:

natural products such as tree moss absolute, basil oil, tropical fruit oils (such as bergamot oil, mandarin oil, etc.), mastix absolute, myrtle oil, palmarosa oil, patchouli oil, petitgrain oil, wormwood oil, lavender oil, rose oil, jasmine oil, ylang-ylang oil, etc.;

alcohols: farnesol, geraniol, linalool, nerol, phenylethyl alcohol, rhodinol, cinnamic alcohol, (Z)-hex-3-en-1-ol, menthol, a-terpineol, etc.;

aldehydes such as citral, alpha-hexyl cinnamaldehyde, Lilial, methylionone, verbenone, nootkatone, geranylacetone, etc.;

esters such as allyl phenoxyacetate, benzyl salicylate, cinnamyl propionate, citronellyl acetate, decyl acetate, dimethylbenzylcarbinyl acetate, dimethylbenzylcarbinyl butyrate, ethyl acetoacetate, cis-3-hexenyl isobutyrate, cis-3-hexenyl salicylate, linalyl acetate, methyl dihydrojasmonate, styralyl propionate, vetiveryl acetate, benzyl acetate, geranyl acetate, etc.;

lactones such as gamma-undecalactone, delta-decalactone, pentadecanolide, 12-oxahexadecanolide, etc.;

acetals such as Viridine (phenylacetaldehyde dimethylacetal), etc.;

and other components often used in perfumery such as indole, p-mentha-8-thiol-3-one, methyleugenol, eugenol, anethol, etc.

Colorants

Generally, for the coloration of hair care compositions according to the invention all substances are suitable which have an absorption in the visible light of electromagnetic radiation (400-4000 nm) The absorption is often caused by the following chromophores: Azo- (mono-, di-, tris-, or poly-) stilbene-, carotenoide-, diarylmethane-, triarylmethane-, xanthene-, acridine-, quinoline-, methine- (also polymethine-) thiazol-, indamine-, indophenol-, azin-, oxazine-, thiazine-, anthraquinone- indigo-, phthalocyanin and further synthetic, natural and/or inorganic chromophores.

FD&C and D&C which can be used in hair care compositions according to the invention are e.g. curcumin, riboflavin, lactoflavin, tartrazine, chinolinyellow, cochenille, azorubin, amaranth, ponceau 4R, erythrosine, red 2G, indigotin, chlorophyll, chlorophyllin, caramel, carbo medicinalis, carotenoids, carotin, bixin, norbixin, annatto, orlean, capsanthin, capsorubin, lycopin, xanthophyll, flavoxanthin, lutein, kryptoxanthin, rubixanthin, violaxanthin, rhodoxanthin, canthaxanthin, betanin, anthocyans without being limited thereto. Examples of dyes are e.g. inorganic pigments such as iron oxide (iron oxide red, iron oxide yellow, iron oxide black etc.) ultramarines, chromium oxide green or carbon black. Other colorants and dyes which can be stabilized with the stabilizing composition according to the invention comprise natural or synthetic organic pigments, disperse dyes which may be solubilized in solvents like direct hair dyes of the HC type, for example HC red No. 3, HC Blue No. 2 and all other hair dyes listed in International Cosmetic Ingredient Dictionary Handbook 7$^{th}$ edition 1997) or the dispersion dyes listed in Color Index International Society of Dyers and Colorist, color varnishes (insoluble salts of soluble dyes, like many Ca-, Ba- or Al-salts of anionic dyes), soluble anionic or cationic dyes such as acid dyes (anionic), basic dyes (cationic), direct dyes, reactive dyes or solvent dyes, fluorescent dyes, fluorescein and isothiocyanates.

Active Ingredients

Active ingredients which might be used in hair care compositions according to the invention comprise vitamins and their derivatives such as tocopherol, ascorbic acid, ascorbyl phosphate, vitamin Q, D, and K, retinol, retinal, retinoic acid, retinol acetate, retinol palmitate, biotin, carotinoid derivatives such as beta carotene, lycopene, asthaxanthene, vegetable extracts, antibacterial ingredients, instable amino acids comprising dipeptides, oligopeptides and polypeptides such as methionin, cysteine, cystine, tryptophan, phenylalanine, tyrosine, phenols, polyphenols or flavanoids, bisabolol, allantoin, phytantriol, panthenol, AHA acids, ubichinones such as Coenzym Q 10, ceramides, pseudoceramides, essential oils, plant extracts, deoxyribonucleic acid, protein hydrolysates.

Preferably the hair care compositions according to the invention are in the form of cosmetic hair-treatment preparations, e.g. hair-washing preparations in the form of shampoos and conditioners, hair-care preparations, e.g. pre-treatment preparations, hair tonics, styling creams, styling gels, pomades, hair rinses, treatment packs, intensive hair treatments e.g. leave-on and rinse-off deep conditioners, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or chamomile.

Based on the application the hair care preparations may be in the form of a (aerosol) spray, (aerosol) foam, gel, gel spray, cream, lotion, liquid or a wax. Hair sprays comprise as well aerosol sprays as pump sprays without propellant. Hair foams comprise as well aerosol foams as pump foams without propellant. Hair sprays and hair foams comprise mainly or exclusively water soluble or water dispersible components. If the components used in hair sprays or hair foams according to the invention are water dispersible, then they may be in the form of micro dispersions with particle sizes of usually 1-350 nm, preferably 1-250 nm. The solid content of such preparations is typically in the range of 0.5 to 20 wt. % of the total weight of the preparation. Such micro dispersions normally do not need further emulsifiers or tensides for their stabilization.

A preferred hair care composition comprises:
1. 0.2 to 20 wt. % of a condensation polymer;
2. 30 to 99.5 wt. %, preferably 40 to 99 wt. %, of at least one solvent chosen from water, water-miscible solvents and mixtures thereof;
3. 0 to 70 wt. % of propellant;
4. 0 to 10 wt. % of at least one water-soluble or water-dispersible hair polymer which is different from 1.);
5. 0 to 0.3% by weight of at least one water-insoluble silicone;
6. 0 to 0.5 wt. % of at least one wax, preferably at least one fatty acid amide;
7. customary additives.

The hair care compositions according to the invention can comprise, as component 4), at least one other water-soluble or water-dispersible hair polymer. The content of this component is then generally from about 0.1 to 10% by weight, based on the total weight of the composition. Here, it is preferable to use water-soluble or water-dispersible polyurethanes which, if desired, additionally comprise siloxane groups in copolymerized form.

The composition according to the invention can comprise, as component 5), at least one water-insoluble silicone, in particular a polydimethylsiloxane, e.g. the Abil® grades from Goldschmidt. The content of this component is then generally from about 0.0001 to 0.2% by weight, preferably from 0.001 to 0.1% by weight, based on the total weight of the composition. Preference is given to using at least one fatty acid amide, such as, for example, erucamide, as component 6).

The hair care compositions according to the invention can, where appropriate, additionally comprise an antifoam, e.g. based on silicone. The amount of antifoam is generally up to 0.001% by weight, based on the total amount of the composition. The compositions according to the invention have the advantage that, on the one hand, they impart the desired hold to the hair and, on the other hand, the polymers are easy to wash out (redispersible). Generally, a natural appearance and shine is imparted to the hair, even when the hair is by its very nature especially thick and/or dark.

In particular, the hair care compositions according to the invention can be formulated to give hair-treatment compositions, in particular hairsprays, with a high propellant content. Advantageously, the hair-treatment compositions according to the invention essentially do not have a "flaking" effect.

In a preferred embodiment, the hair care compositions according to the invention comprise:
1. 0.05 to 20 wt. % of at least one condensation polymer;
2. 20 to 99.95 wt. % of water and/or alcohol;
3. 0 to 79.5 wt. % of customary additives;

The term alcohols refers to all alcohols usually used in cosmetics such as ethanol, n-propanol, isopropanol without being limited thereto.

Other ingredients are cosmetic adjuvants and additives such as propellants, anti-foaming agents, surface active ingredients e.g. tensides, emulsifiers, foam former and solubilisators. The used surface active ingredients may be anionic, cationic, amphoteric or neutral. Further ingredients may be preservatives, antioxidants, perfume oils, lipidic refatters, active and/or caring ingredients such as panthenol, collagen, vitamins, protein hydrolysates, alpha- and beta hydroxylcarbonic acids, stabilisators, pH regulators, opacifiers, colorants, dyes, gel formers, salts, moisturizers, complex formers, viscosity regulators or light screening agents without being limited thereto. Furthermore all known styling- and conditioning polymers can be used in combination with the condensation polymers in order to obtain special effects.

As traditional polymers the above mentioned cationic-, anionic-, neutral-, non-ionic and amphoteric polymers may be used which are included explicitly herein.

In order to obtain certain properties the hair care compositions may additionally comprise conditioning compounds on silicone basis such as polyalkylsiloxane, polyarylsiloxane, polyarylalkylsiloxane, silicone resins, polyethersiloxane or dimethicon copolyole (CTFA) and amino functionalized silicone compounds such as amodimethicone (CTFA), GP 4 Silicone Fluid® and GP 7100® (Genesee), Q2 8220® (Dow Corning), AFL 40® (Union Carbide) or polymers as disclosed in EP-B 852 488.

Other suitable ingredients comprise silicone propfpolymers having a polymeric silicone backbone and non-silicone containing side chains or a non silicone containing polymeric backbone and silicone side chains such as Luviflex® Silk or polymers disclosed in EP-B 852 488.

Preferred hair care compositions according to the invention containing the condensation polymer are hair styling compositions such as hair sprays and hair foams.

In a preferred embodiment these compositions comprise:
1. 0.1 to 10 wt. % of at least one condensation polymer;
2. 20 to 99 wt. % water and/or alcohol;
3. 0 to 70 wt. % of at least one propellant;
4. 0 to 20 wt. % of customary additives;

Propellants for hair sprays or aerosol foams are typically used propellants. Preferred are mixtures of propane/butane, pentane, dimethylether, 11-difluoroethane (HFC-152a), carbon dioxide, nitrogen or compressed air.

A preferred composition for aerosol foams comprises:
1. 0.1 to 10 wt. % of at least on condensation polymer;
2. 55 to 99.8 wt. % water and/or alcohol;
3. 3 to 20 wt. % of a propellant;
4. 0.1 to 5 wt. % of an emulsifier;
5. 0 to 10 wt. % of customary additives.

Emulsifiers for aerosol foams may be all conventionally used non-ionic, cationic, anionic or amphoteric emulsifier.

Examples of non-ionic emulsifiers comprise (INCI)-nomenclature) Laureths, e.g. Laureth-4; Cetheths, e.g. Cetheth-1, polyethylenglycolcetylether; cetheareths, e.g. cetheareth-25, polyglycole fatty acid glycerides, hydroxylated lecithins, lactyl esters of fatty acids, alkylpolyglycosides.

Examples of cationic emulsifiers are cetyldimethyl-2-hydroxyethylammonium-dihydrogenphosphate, cetyltrimonium chloride, cetyltrimonium bromide, cocotrimonium-methylsulfate, quaternium-1 to x (INCI).

Anionic emulsifiers can be selected from alkylsulfate, alkylethersulfate, alkylsulfonate, alkylarylsulfonate, alkylsuccinate, alkylsulfosuccinate, N-alkoylsarcosinate, acyltaurate, acylisethionate, alkylphosphate, alkyletherphosphate, alkylethercarboxylate, alpha-olefinsulfonate, especially the alkali-und earth alkali salts, e.g. sodium, potassium, magnesium, calcium, as well as ammonium- and triethanol amine-salts. The alkylethersulfate, alkyletherphosphate and alkylethercarboxylate may comprise between 1 to 10 ethylenoxide or propylenoxide units, preferably 1 to 3 ethylenoxide-units per molecule.

Preferred hair care compositions comprise hair gels. Such hair gels comprise exemplary:
1. 0.1 to 20 wt. % preferably 1 to 10 wt. % of at least one condensation polymer;
2. 0 to 10 wt. % of at least one carrier (solvent), selected from $C_2$-$C_5$ alcohols, preferably ethanol;
3. 0.01 to 5 wt. %, preferably 0.2 to 3 wt. % of at least one thickener;
4. 0 to 50 wt. % of a propellant;
5. 0 to 10 wt. %, preferably 0.1 to 3 wt. % of a styling polymer different to 1.), preferably a water soluble non-ionic polymer;
6. 0 to 1 wt. % of at least one refatter, preferably selected from glycerine and glycerine derivatives;
7. 0 to 30 wt. % of other customary additives e.g. a silicone component;
8. water and 100 wt. %

An exemplary styling gel can be comprised as follows:
1. 0.1 to 10 wt. % of a condensation polymer;
2. 60 to 99.85 wt. % of water and/or alcohol;
3. 0.05 to 10 wt. % of a gel former;
4. 0 to 20 wt. % of other customary additives.

As gel formers all typically cosmetic gel formers can be used such as slightly cross linked polyacrylic acid e.g. Carbomer (INCI), cellulose derivatives, polysaccharides e.g. xanthan gum, capryl/caprin triglyceride, sodiumacrylate-copolymers, polyquaternium-32 (and) paraffinum liquidum (INCI), sodiumacrylate-copolymers (and) paraffinum liquidum (INCI) (and) PPG-1 trrideceth-6, polyquaternium-37 (and) propyleneglycoldicapratdicarylate (and) PPG-1 trrideceth-6, polyquaternium-7, polyquaternium-44.

Preferred hair care compositions are shampoo preparations comprising the condensation polymer as strengthening and/or conditioning agent.

Preferred shampoo preparations comprise:
1. 0.05 to 10 wt. % of a condensation polymer;
2. 25 to 94.95 wt. % of water;
3. 5 to 50 wt. % of tenside;
4. 0 to 5 wt. % of an additional conditioning agent;
5. 0 to 10 wt. % other customary additives.

All typically used anionic, neutral, amphoteric or cationic tensides may be used within the shampoo preparations.

Exemplary anionic tensides comprise alkylsulfate, alkylethersulfate, alkylsulfonate, alkylarylsulfonate, alkylsuccinate, alkylsulfosuccinate, N-alkoylsarcosinate, acyltaurate, acylisethionate, alkylphosphate, alkyletherphosphate, alkylethercarboxylate, alpha-olefinsulfonate, especially the alkali-und earth alkali salts, e.g. sodium, potassium, magnesium, calcium, as well as ammonium- and triethanol amine-salts. The alkylethersulfate, alkyletherphosphate and alkylethercarboxylate may comprise between 1 to 10 ethylenoxide or propylenoxide units, preferably 1 to 3 ethylenoxide-units per molecule.

Suitable are e.g. sodium laurysulfate, ammonium laury sulfate, sodium laurylethersulfate, ammonium laurylethersulfate, sodium lauroylsarconisate, sodiumoleylsuccinate, ammonium laurylsulfosuccinate, sodium dodecylbenzolsulfonate, triethanolamidodecylbenzolsulfonate.

Suitable amphoteric tensides are e.g. alkylbetaine, alkylamidopropylbetaine, alkylsulfobetaine, alkylglycinate, alkylcarboxyglycinate, alkylamphoacetate or propionate, alkylamphodiacetate or dipropionate such as cocodimethylsulfopropylbetain, laurylbetain, cocamidopropylbetaine or sodium cocamphopropionate.

Examples of non ionic tensides are e.g. reaction products of aliphatic alcohols or alkylphenols with 6 to 20 C-Atoms of a linear or branched alkyl chain with ethylenoxide and/or propylenoxide. The amount of alkylenoxide is about 6 to 60 mole to one mol alcohol. Furthermore alkylaminoxide, mono- or dialkylalkanolamide, fatty esters of polyethylene glycols, alkylpolyglycosides or sorbitanether ester are suitable for the incorporation of hair care compositions according to the invention.

Furthermore, the shampoo preparations may contain the usual cationic tensides such as quaternized ammonium compounds e.g. cetyltrimethylammoniumchlorid or bromide (INCI: cetrimoniumchloride or bromide), hydroxyethylcetyldimonium phosphate (INCI: Quaternium-44), Luviquat® Mono LS (INCI: Cocotrimoniummethosulfate), poly (oxy-1,2-Ethandiyl), (Octadecylnitrilio) tri-2,1-Ethandiyl) tris-(hydroxy)-phosphate (INCI Quaternium-52).

For special effects typical conditioning agents may be combined with the condensation polymers within the shampoo preparations such as the previously mentioned cationic polymers named polyquaternium (INCI), especially copolymers of vinylpyrrolidone/N-vinylimidazolium salts (Luviquat® FC, Luviquate HM, Luviquat® MS, Luviquat® Ultracare), copolymers of N-vinylpyrrolidone/dimethylaminoethylmethacrylate quaternized with diethylsulfate (Luviquat® PQ 11), copolymers of N-cationic cellulose derivatives (Polyquaternium-4 and -10), acrylamidecopolymers (Polyquaternium-7). Furthermore protein hydrolysates may be used as well as conditioning agents on silicone basis such as polyarylsiloxane, polyarylalkylsiloxane, polyethersiloxane or silicone resins. Other suitable silicone compounds are dimethicondopolyole (CTFA) and amino functionalised silicone derivatives such as amodimethicone (CTFA). Furthermore cationic guar derivatives such as guarhydroxypropyltrimoniumchloride (INCI) may be used.

Preferred hair care compositions are hair treatment preparations such as rinse off- and leave on-conditioners comprising the condensation polymer as strengthening and/or conditioning agent.

Preferred conditioner preparations comprise:
1. 0.05-10 wt. % of a condensation polymer;
2. 25-94.95 wt. % of water;
3. 0.1-30 wt. % of tensides/emulsifier/surface active ingredient;
4. 0.1-30 wt. % of oil/emollient;
5. 0-5 wt. % of an additional conditioning agent;
6. 0-10 wt. % other customary additives.

All typically used anionic, neutral, amphoteric or cationic tensides may be used within the conditioner preparations.

Exemplary anionic tensides comprise alkylsulfate, alkylethersulfate, alkylsulfonate, alkylarylsulfonate, alkylsuccinate, alkylsulfosuccinate, N-alkoylsarkosinate, acyltaurate, acylisethionate, alkylphosphate, alkyletherphosphate, alkylethercarboxylate, alpha-olefinsulfonate, especially the alkali-und earth alkali salts, e.g. sodium, potassium, magnesium, calcium, as well as ammonium- and triethanol amine-salts. The alkylethersulfate, alkyletherphosphate and alkylethercarboxylate may comprise between 1 to 10 ethylenoxide or propylenoxide units, preferably 1 to 3 ethylenoxide-units per molecule.

Suitable are e.g. sodium laurylsulfate, ammonium lauryl sulfate, sodium laurylethersulfate, ammonium laurylethersulfate, sodium lauroylsarkonisate, sodiumoleylsuccinate, ammonium laurylsulfosuccinate, sodium dodecylbenzolsulfonate, triethanolamidodecylbenzolsulfonate.

Suitable amphoteric tensides are e.g. alkylbetaine, alkylamidopropylbetaine, alkylsulfobetaine, alkylglycinate, alkylcarboxyglycinate, alkylamphoacetate or propionate, alkylamphodiacetate or dipropionate such as cocodimethylsulfopropylbetain, laurylbetain, cocamidopropylbetain or sodium cocamphopropionate.

Examples of non ionic tensides are e.g. reaction products of aliphatic alcohols or alkylphenols with 6 to 20 C-Atoms of a linear or branched alkyl chain with ethylenoxide and/or propylenoxide. The amount of alkylenoxide is about 6 to 60 mole to one mol alcohol. Furthermore alkylaminoxide, mono- or dialkylalkanolamide, fatty esters of polyethylen glycols, alkylpolyglycosides or sorbitanether ester are suitable for the incorporation of hair care compositions according to the invention.

Furthermore, the conditioner preparations may contain the usual cationic tensides such as quaternised ammonium compounds e.g. cetyltrimethylammoniumchlorid or bromide (INCI: cetrimoniumchloride or bromide), hydroxyethylcetyldimonium phosphate (INCI: Quaternium-44), Luviquat® Mono LS (INCI: Cocotrimoniummethosulfate), poly (oxy-1,2-Ethandiyl), (Octadecylnitrilio) tri-2,1-Ethandiyl) tris-(hydroxy)-phosphate (INCI Quaternium-52).

For special effects typical conditioning agents may be combined with the condensation polymers within the conditioning preparations such as the previously mentioned cationic polymers named polyquaternium (INCI), especially copolymers of vinylpyrrolidone/N-vinylimidazolium salts (Luviquat® FC, Luviquat® HM, Luviquat® MS, Luviquat® Ultracare), copolymers of N-vinylpyrrolidone/dimethylaminoethylmethacrylate quaternised with diethylsulfate (Luviquat® PQ 11), copolymers of N-cationic cellulose derivatives (Polyquaternium-4 and -10), acrylamidcopolymers (Polyquaternium-7). Furthermore protein hydrolysates may be used as well as conditioning agents on silicone basis such as polyarylsiloxane, polyarylalkylsiloxane, polyethersiloxane or silicone resins. Other suitable silicone compounds are dimethicondopolyole (CTFA) and amino functionalised silicone derivatives such as amodimethicone (CTFA). Furthermore cationic guar derivatives such as guarhydroxypropyltrimoniumchloride (INCI) may be used.

Furthermore, the conditioner preparations may contain the usual surface active ingredients like emulsifiers, solubilizers and the like. An emulsifier enables two or more immiscible components to be combined homogeneously. Moreover, the emulsifier acts to stabilize the composition. Emulsifiers that may be used in the present invention in order to form O/W, W/O, O/W/O or W/O/W emulsions/microemulsions include sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polyglyceryl-4 oleate/PEG-8 propylene glycol cocoate, oleamide DEA, TEA myristate, TEA stearate, magnesium stearate, sodium stearate, potassium laurate, potassium ricinoleate, sodium cocoate, sodium tallowate, potassium castorate, sodium oleate, and mixtures thereof. Further exemplary emulsifiers are phosphate esters and the salts thereof such as cetyl phosphate (Amphisol® A), diethanolamine cetyl phosphate (Amphisol®), potassium cetyl phosphate (Amphisol® K), sodium glyceryl oleate phosphate, hydrogenated vegetable glycerides phosphate and mixtures thereof. Furthermore, one or more synthetic polymers may be used as an emulsifier. For example, PVP eicosene copolymer, acrylates/$C_{10-30}$ alkyl acrylate crosspolymer, acrylates/steareth-20 methacrylate copolymer, PEG-22/dodecyl glycol copolymer, PEG-45/dodecyl glycol copolymer, and mixtures thereof. Further exemplary emulsifiers are fatty alcohols, e.g. cetearyl alcohol (Lanette O, Cognis Coopearation), cethyl alcohol (Lanette 16, Cognis Cooperation), stearyl alcohol (Lanette 18, Cognis Coopearation), Laneth-5 (Polychol 5, Croda Chemicals), furthermore sucrose and glucose derivatives, e.g. sucrose distearate (Crodesta F-10, Croda Chemicals), Methyl glucose isostearate (Isolan IS, Degussa Care Chemicals), furthermore ethoxylated carboxylic acids or polyethyleneglycol esters and polyethyleneglycol ethers, e.g. steareth-2 (Brij 72, Uniqema), steareth-21 (Brij 721, Uniqema), ceteareth-25 (Cremophor A25, BASF Cooperation), PEG-40 hydrogenated castor oil (Cremophor RH-40, BASF Cooperation), PEG-7 hydrogenated castor oil (Cremophor WO7, BASF Cooperation), PEG-30 Dipolyhydroxystearate (Arlacel P 135, Uniqema), furthermore glyceryl esters and polyglyceryl esters, e.g. polyglyceryl-3-diisostearate (Hostacerin TGI, Clariant Cooperation), polyglyceryl-2 dipolyhydroxystearate (Dehymuls PGPH, Cognis Cooperation), polyglyceryl-3 methylglucose distearate (Tego Care 450, Degussa Care Chemicals). The preferred emulsifiers are cetyl phosphate (Amphisol® A), diethanolamine cetyl phosphate (Amphisol®), potassium cetyl phosphate (Amphisol® K), PVP Eicosene copolymer, acrylates/$C_{10-30}$-alkyl acrylate crosspolymer, PEG-20 sorbitan isostearate, sorbitan isostearate, and mixtures thereof. The one or more emulsifiers are present in a total amount of at least 0.01 wt. % of the total weight of the composition. Preferably about 0.01 wt. % to about 20 wt.

% of the total weight of the composition of the present invention is used. Most preferred, about 0.1 wt. % to about 10 wt. % of emulsifiers are used.

Furthermore, the conditioner preparations may contain the usual oily and fatty components may be chosen from mineral oils and mineral waxes; oils such as triglycerides of caprinic acid and/or caprylic acid or castor oil; oils or waxes and other natural or synthetic oils, in an preferred embodiment esters of fatty acids with alcohols e.g. isopropanol, propyleneglycol, glycerin or esters of fatty alcohols with carbonic acids or fatty acids; alkylbenzoates; and/or silicone oils.

Exemplary fatty substances which can be incorporated in the oil phase of the emulsion, microemulsion, oleo gel, hydrodispersion or lipodispersion of the present invention are advantageously chosen from esters of saturated and/or unsaturated, linear or branched alkyl carboxylic acids with 3 to 30 carbon atoms, and saturated and/or unsaturated, linear and/or branched alcohols with 3 to 30 carbon atoms as well as esters of aromatic carboxylic acids and of saturated and/or unsaturated, linear or branched alcohols of 3-30 carbon atoms. Such esters can advantageously be selected from octylpalmitate, octylcocoate, octylisostearate, octyldodecylmyristate, cetearylisononanoate, isopropylmyristate, isopropylpalmitate, isopropylstearate, isopropyloleate, n-butylstearate, n-hexyllaurate, n-decyloleate, isooctylstearate, isononylstearate, isononylisononanoate, 2-ethyl hexylpalmitate, 2-ethylhexyllaurate, 2-hexyldecylstearate, 2-octyldodecylpalmitate, stearylheptanoate, oleyloleate, oleylerucate, erucyloleate, erucylerucate, tridecylstearate, tridecyltrimellitate, as well as synthetic, half-synthetic or natural mixtures of such esters e.g. jojoba oil.

Other fatty components suitable for conditioner preparations of the present invention include polar oils such as lecithins and fatty acid triglycerides, namely triglycerol esters of saturated and/or unsaturated, straight or branched carboxylic acid with 8 to 24 carbon atoms, preferably of 12 to 18 carbonatoms whereas the fatty acid triglycerides are preferably chosen from synthetic, half synthetic or natural oils (e.g. cocoglyceride, olive oil, sun flower oil, soybean oil, peanut oil, rape seed oil, sweet almond oil, palm oil, coconut oil, castor oil, hydrogenated castor oil, wheat oil, grape seed oil, macadamia nut oil and others); apolar oils such as linear and/or branched hydrocarbons and waxes e.g. mineral oils, vaseline (petrolatum); paraffins, squalane and squalene, polyolefins, hydrogenated polyisobutenes and isohexadecanes, favored polyolefins are polydecenes; dialkyl ethers such as dicaprylylether; linear or cyclic silicone oils such as preferably cyclomethicone (octamethylcyclotetrasiloxane; cetyldimethicone, hexamethylcyclotrisiloxane, polydimethylsiloxane, poly(methylphenylsiloxane) and mixtures thereof.

Other fatty components which can advantageously be incorporated in conditioner preparations of the present invention are isoeikosane; neopentylglycoldiheptanoate; propyleneglycoldicaprylate/dicaprate; caprylic/capric/diglycerylsuccinate; butyleneglycol caprylat/caprat; $C_{12-13}$-alkyllactate; di-$C_{12-13}$-alkyltartrate; triisostearin; dipentaerythrityl hexacaprylat/hexacaprate; propyleneglycolmonoisostearate; tricaprylin; dimethylisosorbid. Especially beneficial is the use of mixtures $C_{12-15}$-alkylbenzoate and 2-ethylhexylisostearate, mixtures $C_{12-15}$-alkylbenzoate and isotridecylisononanoate as well as mixtures of $C_{12-15}$-alkylbenzoate, 2-ethylhexylisostearate and isotridecylisononanoate.

The oily phase of the conditioner preparation can also contain natural vegetable or animal waxes such as bees wax, china wax, bumblebee wax and other waxes of insects as well as shea butter and cocoa butter.

Suitable silicone oils are e.g. dimethylpolysiloxane, diethylpolysiloxane, diphenylpolysiloxane, cyclic siloxanes, poly (methylphenylsiloxanes) as well as amino-, fatty acid-, alcohol-, polyether-, epoxy-, fluor-, glycoside-, and/or alkyl modified silicone compounds which are liquid or solid at room temperature and mixtures thereof. The number average molecular weight of the dimethicones and poly(methylphenylsiloxanes) is preferably in the range of 100 to 150000 g/mol. Preferred cyclic siloxanes comprise 4- to 8-membered rings which are for example commercially available as cyclomethicones.

In all hair care preparations described above the sum of the ingredients adds to 100%.

The following examples are provided to further illustrate the processes and compositions of the present invention. These examples are illustrative only and are not intended to limit the scope of the invention in any way. (Mn denotes the number average molecular weight)

EXAMPLE 1

Synthesis of a Tertiary Amine Functional Hyper Branched Polyester Amide 305 g of bis-(N,N-dimethyl aminopropyl) amine and 350 g of molten hexahydro phthalic anhydride were added to a glass reactor equipped with stirrer and condenser, and which can be heated by oil. The mixture was slowly heated to 180° C. and ½ h after the start, 145 g molten diisopropanolamine was added and 1½ h later vacuum was applied to remove the reaction water. After 5 h the mixture was cooled and a glassy polymer with a Mn=1600 was obtained.

EXAMPLE 2

Synthesis of a Tertiary Amine Functional Hyper Branched Polyester Amide 248 g of bis-(N,N-dimethyl aminopropyl) amine and 379 g of molten hexahydro phthalic anhydride were added to a glass reactor equipped with stirrer and condenser, and which can be heated by oil. The mixture was slowly heated to 180° C. and ½ h after the start, 172 g molten diisopropanolamine was added and 1½ h later vacuum was applied to remove the reaction water. After 5 h the mixture was cooled and a glassy polymer with a Mn=3400 was obtained.

EXAMPLE 3

Synthesis of a Tertiary Amine Functional Hyper Branched Polyester Amide 232 g of bis-(N,N-dimethyl aminopropyl) amine and 458.1 g of molten dodecenyl succinic anhydride were added to a glass reactor equipped with stirrer and condenser, and which can be heated by oil. The mixture was slowly heated to 180° C. and ½ h after the start, 172 g molten diisopropanolamine was added and 1½ h later vacuum was applied to remove the reaction water. After 5 h the mixture was cooled and a viscous polymer was obtained.

EXAMPLE 4

Synthesis of a Tertiary Amine Functional Hyper Branched Polyester Amide 360.7 g of bis-(N,N-dimethyl aminopropyl) amine and 268.1 g of succinic anhydride were added to a glass reactor equipped with stirrer and condenser, and which can be heated by oil. The mixture was slowly heated to 180° C. and ½ h after the start, 171.3 g molten diisopropanolamine was added and 1½ h later vacuum was applied to remove the reaction water. After 5 h the mixture was cooled and a glassy polymer was obtained.

EXAMPLE 5

Synthesis of a Tertiary Amine and Morpholine Amide Functional Hyper Branched Polyester Amide 189 g of bis-(N,N-dimethyl aminopropyl) amine, 88 g morpholine and 389 g of molten hexahydro phthalic anhydride were added to a glass reactor equipped with stirrer and condenser, and which can be heated by oil. The mixture was slowly heated to 180° C. and ½ h after the start, 134 g molten diisopropanolamine was added and 1½ h later vacuum was applied to remove the reaction water. After 5 h the mixture was cooled and a glassy polymer was obtained.

EXAMPLE 6

Synthesis of a Piperazine Amide Functional Hyper Branched Polyester Amide 244.1 g of N-methyl piperazine was added to a glass reactor equipped with stirrer and condenser, and which can be heated by oil. Next 339.2 g succinic anhydride was added and the mixture was slowly heated to 120° C. ½ h after the start, 216.7 g diisopropanolamine was added and the mixture was heated to 180° C. After 72 h vacuum was applied to remove the reaction water. After 5 h the mixture was cooled and a glassy polymer was obtained.

EXAMPLE 7

Synthesis of a Tertiary Amine Functional Linear Polyester Amide 196.3 g of bis-(N,N-dimethyl aminopropyl) amine and 376.6 g of molten succinic anhydride were added to a glass reactor equipped with stirrer and condenser, and which can be heated by oil. The mixture was slowly heated to 180° C. and ½ h after the start, 236.1 g 2-methylamine ethanol was added and 1½ h later vacuum was applied to remove the reaction water. After 5 h the mixture was cooled and a glassy polymer was obtained.

EXAMPLE 8

Synthesis of a Quaternary Amine Functional Hyper Branched Polyester amide 50 g of the polymer of example 1 was dissolved in 50 g water and at room temperature 13.1 g of dimethyl sulphate was slowly added. First the mixture was turbid but within 10 min the temperature raised to about 50° C. and the mixture became clear. After 24 h the fully quaternized polymer solution was ready for use.

EXAMPLE 9

Synthesis of a Partially Quaternary Amine Functional Hyper Branched Polyester Amide 50 g of the polymer of example 1 was dissolved in 50 g water and at room temperature 6.5 g of dimethyl sulphate was slowly added. First the mixture was turbid but within 10 min the temperature raised to about 50° C. and the mixture became clear. After 24 h the 50% quaternized polymer solution was ready for use.

EXAMPLE 10

Synthesis of a Quaternary Amine Functional Hyper Branched Polyester Amide 50 g of the polymer of example 2 was dissolved in 50 g acetonitrile. At room temperature 22.3 g of methyl iodide was slowly added. First the mixture was turbid but within 10 min the temperature raised to about 50° C. and the mixture became clear again. After 24 h the quaternized polymer solution was ready for use.

EXAMPLE 11

Synthesis of a Quaternary Amine Functional Hyper Branched Polyester Amide 50 g of the polymer of example 3 was dissolved in 50 g water and at room temperature 13.1 g of dimethyl sulphate was slowly added. First the mixture was turbid but within 10 min the temperature raised to about 50° C. and the mixture became clear. After 24 h the fully quaternized polymer solution was ready for use.

EXAMPLE 12

Synthesis of a Quaternary Amine Functional Hyper Branched Polyester Amide 50 g of the polymer of example 4 was dissolved in 50 g water and at room temperature 13.1 g of dimethyl sulphate was slowly added. First the mixture was turbid but within 10 min the temperature raised to about 50° C. and the mixture became clear. After 24 h the fully quaternized polymer solution was ready for use.

EXAMPLE 13

Synthesis of a Piperazine Methyl Quaternized Functional Hyper Branched Polyester Amide 50 g of the polymer of example 6 was dissolved in 50 g water and at room temperature 19.6 g of dimethyl sulphate was slowly added. First the mixture was turbid but within 10 min the temperature raised to about 50° C. and the mixture became clear again. After 24 h the quaternized polymer solution was ready for use.

EXAMPLE 14

Styling Performance

Determination of the styling effect of hair care compositions according to the invention comprising quaternized condensation polymers. The styling properties are determined by measuring the stiffness of hair tresses after treatment with a leave-on formulation (@ 1% active concentration in water/ethanol 80:20).

Hair tresses: Double bleached Caucasian hair, remis, 2 cm wide, 20 cm length, Kerling Gmbh.

Experimental design: Each hair tress was immersed in 20.0 g of the formulation in a closed glass cylinder. The cylinder was shaken horizontally for 1 min. The tresses were then removed, detangled and combed 20 times in a downward motion to remove all excess solution. The tresses were then allowed to dry overnight in ambient conditions. The stiffness was evaluated manually. The stiffness is summarised in the table below. The scale goes from + to +++ whereas +++ expresses very high degree of stiffness.

|  | polymer of example 11 | polymer of example 13 | Placebo |
|---|---|---|---|
| Perceived stiffness of hair tress (dry, before combing) | ++ | ++ | + |

As can be seen from the table, the quaternized hybranes lead to enhanced stiffness relative to placebo treatment which can be advantageously used in styling products.

EXAMPLE 15

Determination of the conditioning effect of hair care compositions according to the invention comprising quaternized condensation polymers by measuring the combability of hair tresses after treatment with a leave-on conditioner (@ 1% active concentration in water/ethanol 80:20).

Hair tresses: Double bleached Caucasian hair, remis, 2 cm wide, 20 cm length, Kerling Gmbh.

Experimental design: Each hair tress was immersed in 20.0 gr Formulation in a closed glass cylinder. The cylinder was shaken horizontally for 1 min. The tresses were then removed, detangled and combed 20 times in a downward motion to remove all excess solution. The tresses were then allowed to dry overnight in ambient conditions. Combability (i.e. the ease of combability) was evaluated manually using a comb. The perceived ease of combing is summarised in the table below. The scale goes from + to +++ whereas +++ expresses very easy combing.

|  | polymer of example 12 | polymer of example 13 | Placebo |
|---|---|---|---|
| Perceived ease of wet combability (upon treatment) | ++ | + | + |
| Perceived ease of dry combability (after treatment) | ++ | ++ | + |

As can be seen from the table, the quaternized hybranes lead to enhanced combing ease relative to placebo treatment.

EXAMPLE 16

| Hair styling spray | |
|---|---|
| INCI Nomenclature | wt. % |
| Alcohol, anhydrous | Ad to 100 |
| Octylacrylamide/acrylate/butylaminoethylmethacrylate copolymer | 2.50 |
| Hydroxypropyl cellulose | 0.50 |
| Aminomethylpropanol | 0.50 |
| Perfume oil | 0.200 |
| Condensation polymer according to the invention | 0.01-20 |

The hydroxypropyl cellulose is first dissolved in half of the alcohol and is subsequently charged with aminomethylpropanol. The other components, with exception of the acrylate resin, are dissolved in alcohol and this solution is added under agitation to the hydroxypropyl cellulose followed by the addition of the acrylate resin.

EXAMPLE 17

| Protective Styling Hair Mousse | |
|---|---|
| INCI Nomenclature | wt. % |
| Aqua (water) | Ad 100 |
| Polyquaternium-4 | 2.00 |
| Cocamidopropylamine Oxide | 0.40 |
| PEG-12 Dimethicone | 0.20 |
| Propylene Glycol & Diazolidinyl Urea & Methylparaben & Propylparaben | 1.00 |
| Perfume oil | 0.20 |
| Propane/Butane | 10.00 |
| Condensation polymer according to the invention | 0.01-20 |

Add the ingredients in the order shown under agitation. Afterwards, charge adequate containers with propane/butane.

EXAMPLE 18

| Clear Shampoo | | |
|---|---|---|
| | INCI Nomenclature | wt. % |
| 1 | Sodium Laureth Sulfate | 15.00 |
| | PEG-7 Glyceryl Cocoate | 3.00 |
| | Cocamidopropyl Betaine | 2.50 |
| | Tocopheryl Acetate | 0.10 |
| | *Borago Officinalis* Seed Oil & Tocopherol & Ascorbyl Palmitate | 0.30 |
| | PEG-40 Hydrogenated Castor Oil | 4.00 |
| | Perfume oil | 0.30 |
| | BHT | 0.05 |
| 2 | Panthenol | 1.00 |
| | Disodium EDTA | 0.10 |
| | Aqua (water) | Ad 100 |
| | Methylchloroisothiazolinone & Methylisothiazolinone | 0.10 |
| | Condensation polymer according to the invention | 5.00 |
| 3 | Sodium Chloride | 2.00 |
| | PEG-150 Pentaerythrityl Tetrastearate | 3.00 |

Add all ingredients of part 1) and mix intensively until a homogeneous solution is obtained. Then, add the water under slow agitation and wait until the foam has disappeared. Finally, add carefully the thickening agent like Sodium Chloride or Crothix LVR.

EXAMPLE 19

| Hydrating Shampoo | | |
|---|---|---|
| | INCI Nomenclature | wt. % |
| 1 | Sodium Laureth Sulfate | 12.00 |
| | Ethylhexyl Methoxycinnamate | 0.30 |
| | Methylchloroisothiazolinone & Methylisothiazolinone | 0.10 |
| | Panthenol | 1.00 |
| | PEG-7 Glyceryl Cocoate | 2.00 |
| | Cocamidopropyl Betaine | 5.00 |
| | Glycol Distearate & Glycerin and Laureth-4 & Cocamidopropyl Betaine | 2.00 |
| | Disodium EDTA | 0.10 |
| | Parfum | 0.80 |

Hydrating Shampoo

| | INCI Nomenclature | wt. % |
|---|---|---|
| | Polyquaternium-10 | 0.10 |
| | Decyl Glucoside | 5.00 |
| 2 | Sodium Chloride | 1.50 |
| | Condensation polymer according to the invention | 4.00 |
| | PEG-18 Glyceryl Oleate/Cocoate | 1.00 |
| | Aqua (water) | Ad 100 |

Add all ingredients of part 1 and mix intensively until a homogeneous solution is obtained. Add the water under slow agitation and wait until the foam has disappeared. Than add carefully the thickening agent like Sodium Chloride or Crothix LVR.

EXAMPLE 20

Hydrating Shampoo for Color Protection

| | INCI Nomenclature | wt. % |
|---|---|---|
| 1 | Sodium Laureth Sulfate | 12.00 |
| | Polysilicone-15 | 0.30 |
| | Methylchloroisothiazolinone & Methylisothiazolinone | 0.10 |
| | Panthenol | 1.00 |
| | PEG-7 Glyceryl Cocoate | 2.00 |
| | Cocamidopropyl Betaine | 5.00 |
| | Glycol Distearate & Glycerin and Laureth-4 & Cocamidopropyl Betaine | 2.00 |
| | Disodium EDTA | 0.10 |
| | Parfum | 0.80 |
| | Polyquaternium-10 | 0.10 |
| | Decyl Glucoside | 5.00 |
| 2 | Aqua (water) | Ad 100 |
| | Condensation polymer according to the invention | 3.00 |
| | Sodium Chloride | 1.50 |
| | PEG-18 Glyceryl Oleate/Cocoate | 1.00 |

Add all ingredients of part 1 and mix intensively until a homogeneous solution is obtained. Add the water under slow agitation and wait until the foam has disappeared. Than add carefully the thickening agent like Sodium Chloride or Crothix LVR.

EXAMPLE 21

Extra Shine Revitalizing Hair Cream

| | INCI Nomenclature | wt. % |
|---|---|---|
| 1 | Simmondsia Chinensis (Jojoba) Seed Oil | 3.00 |
| | Prunus Armeniaca (Apricot) Kernel Oil | 3.00 |
| | Phenyl Trimethicone | 2.00 |
| | C12-15 Alkyl Benzoate | 2.00 |
| | Glyceryl Stearate SE | 2.00 |
| | Polysilicone-15 | 0.50 |
| | Tocopheryl Acetate | 0.50 |
| | Cetearyl Alcohol | 1.60 |
| 2 | Aqua (water) | Ad 100 |
| | Condensation polymer according to the invention | 2.00 |
| 3 | Behentrimonium Chloride | 1.00 |
| | Cocodimonium Hydroxypropyl Hydrolyzed Wheat Protein | 0.30 |
| | Propylene Glycol & Diazolidinyl Urea & Methylparaben & Propylparaben | 1.00 |

Heat part 1 and part 2 separately to 65° C. under moderate agitation. When both have the same temperature add part 2 into part 1 under agitation. Let cool to 40° C. and add part 3 under agitation, homogenize. Cool to ambient temperature.

EXAMPLE 22

Hair Repair Treatment

| | INCI Nomenclature | wt. % |
|---|---|---|
| A | Cetearyl Octanoate | 0.20 |
| | Phytantriol | 0.10 |
| | PEG-40 Hydrogenated Castor Oil | 2.00 |
| B | Perfume oil | q.s. |
| | Cocotrimonium Methosulfate | 2.00 |
| C | Aqua (water) | Ad 100 |
| D | Polyquaternium-16 | 2.00 |
| | Dimethicone Copolyol | 1.00 |
| | Condensation polymer according to the invention | 3.00 |
| | Alcohol | 10.00 |
| | Citric Acid | q.s. |

EXAMPLE 23

Color Balm

| | INCI Nomenclature | wt. % |
|---|---|---|
| A | Ceteareth-6, Stearyl Alcohol | 1.50 |
| | Ceteareth-25 | 1.50 |
| | Cetearyl Alcohol | 3.00 |
| | Cetearyl Octanoate | 6.00 |
| | Phytantriol | 0.30 |
| B | Polyquaternium-44 | 7.70 |
| | Condensation polymer according to the invention | 3.00 |
| | Propylene Glycol | 2.00 |
| | Panthenol | 1.00 |
| | Perfume oil | q.s. |
| | Aqua (water) | Ad 100 |
| C | C.I. 42510, Basic Violet 14 | 0.05 |
| | C.I. 12245, Basic Red 76 | 0.08 |
| | Preservative | q.s. |
| | Citric Acid | q.s. |

EXAMPLE 24

Silky Hair Cocktail

| | INCI Nomenclature | wt. % |
|---|---|---|
| A | Caprylic/Capric Triglyceride, Acrylates Copolymer | 3.00 |
| | Dimethicone Copolyol | 0.50 |
| | Dimethicone Copolyol | 2.00 |
| | Cyclomethicone, Dimethiconol | 3.00 |
| | Amodimethicone, Cetrimonium Chloride, Trideceth-10 | 2.00 |
| | Phenyl Trimethicone | 2.00 |
| | Macadamia (Ternifloria) Nut Oil | 1.00 |
| | Tocopheryl Acetate | 0.50 |
| | PEG-40 Hydrogenated Castor Oil | 1.00 |
| | Perfume oil | q.s. |
| B | Aqua (water) | Ad 100 |
| | Aminomethyl Propanol | 0.46 |
| | Condensation polymer according to the invention | 3.00 |
| | PEG/PPG-25/25 Dimethicone/Acrylates Copolymer | 4.00 |
| | Preservative | q.s. |

EXAMPLE 25

Oil Sheen Moisturizer

| | INCI Nomenclature | wt. % |
|---|---|---|
| A | Cetyl Alcohol | 2.00 |
| | PEG-75 Lanolin | 1.00 |
| | Glyceryl Stearate | 4.00 |
| | Ceteareth-25 | 1.00 |
| | Cetearyl Octanoate | 4 |
| B | Glycerin | 10.00 |
| | Condensation polymer according to the invention | 5.00 |
| | Propylene Glycol | 2.00 |
| | Cocotrimonium Methosulfate | 1.00 |
| | Trimethylsilylamodimethicone, SM 2115 Octoxynol-40, Isolaureth-6, Glycerin | 1.50 |
| | Polysorbate 20 | 1.00 |
| | Aqua (water) | Ad 100 |
| C | Panthenol | 0.50 |
| | Preservative | q.s. |
| | Perfume oil | q.s. |
| | Citric Acid | q.s. |

EXAMPLE 26

Setting Cream High Gloss

| | INCI Nomenclature | wt. % |
|---|---|---|
| A | Cetyl Alcohol | 5.00 |
| | Glyceryl Stearate SE | 10.00 |
| | Isopropyl Myristate | 5.00 |
| | Preservative | q.s. |
| | Dimethicone | 1.00 |
| B | Glycerin | 5.00 |
| | Condensation polymer according to the invention | 5.00 |
| | Disodium EDTA | 0.20 |
| | PVP | 2.00 |
| | Aqua (water) | Ad 100 |
| C | Perfume oil | q.s. |

EXAMPLE 27

Permanent Wave

| | INCI Nomenclature | wt. % |
|---|---|---|
| A | Aqua (water) | Ad 100 |
| | Condensation polymer according to the invention | 3.00 |
| | Cocamidopropyl Betaine | 0.20 |
| | Polysorbate 20 | 0.20 |
| | Polyquaternium 16 | 1.25 |
| | Disodium EDTA | 0.20 |
| | Hydroxyethylcellulose | 0.20 |
| B | Thioglycolic Acid | 8.00 |
| C | Ammonium Hydroxide | 11.00 |
| D | Ammoniumcarbonat | 5.00 |

EXAMPLE 28

Fixation for Permanent Waves

| | INCI Nomenclature | wt. % |
|---|---|---|
| A | PEG-40 Hydrogenated Castor Oil | 1.00 |
| | Perfume oil | 0.20 |
| | Condensation polymer according to the invention | 2.00 |
| | Aqua (water) | Ad 100 |
| B | Cocamidopropyl Betaine | 0.2 |
| | Ceteareth-25 | 0.20 |
| | Polyquaternium 16 | 2.50 |
| | Preservative | q.s. |
| C | Hydrogen Peroxid | 2.30 |
| D | Phosphoric Acid | q.s. |

EXAMPLE 29

Hair Gel

| INCI Nomenclature | wt. % |
|---|---|
| Carbomer | 0.50 |
| Aqua (water) | Ad 100 |
| Triethanolamine | 0.70 |
| Condensation polymer according to the invention | 6.00 |
| PVP | 5.00 |
| Perfume oil | q.s. |
| PEG-40 Hydrogenated Castor Oil | q.s. |
| Phenoxyethanol, Methylparaben, Butylparaben, Ethylparaben and Propylparaben | 0.10 |
| Tocopheryl Actetate | 0.10 |

Add all ingredients of part 1 and mix intensively until a homogeneous gel is obtained.

EXAMPLE 30

Hair Gel

| INCI Nomenclature | wt. % |
|---|---|
| Condensation polymer according to the invention | 10.00 |
| Polyquaternium-46 | 2.50 |
| Alcohol | 15.00 |
| Aqua (water) | Ad 100 |
| PVP | 5.00 |
| Perfume oil | 0.10 |
| Glycerin | 0.10 |
| Hydroxyethylcellulose | 2.00 |

Add all ingredients of part 1 and mix intensively until a homogeneous gel is obtained.

EXAMPLE 31

Hair Gel

| INCI Nomenclature | wt. % |
|---|---|
| Condensation polymer according to the invention | 6.00 |
| Corn Starch Modified | 2.00 |
| Chitosan | 0.50 |
| Perfume oil | q.s. |
| PEG-40 Hydrogenated Castor Oil | q.s. |

-continued

| Hair Gel | |
|---|---|
| INCI Nomenclature | wt. % |
| PEG-14 Dimethicone | 0.10 |
| Phenoxyethanol, Methylparaben, Butylparaben, Ethylparaben and Propylparaben | 0.10 |
| Aqua (water) | Ad 100 |

Add all ingredients of part 1 and mix intensively until a homogeneous gel is obtained.

EXAMPLE 32

| Hair Gel | |
|---|---|
| INCI Nomenclature | wt. % |
| Carbomer | 0.50 |
| Aqua (water) | Ad 100 |
| Triethanolamine | 0.70 |
| Condensation polymer according to the invention | 3.00 |
| Acrylates/C1-2 Succinates/Hydroxyacrylates Copolymer | 2.00 |
| Aminomethyl Propanol | 0.19 |
| Perfume oil | q.s. |
| PEG-40 Hydrogenated Castor Oil | q.s. |
| PEG-8 | 0.10 |
| Phenoxyethanol, Methylparaben, Butylparaben, Ethylparaben and Propylparaben | 0.10 |
| Hydroxyethylcellulose | 0.50 |

Add all ingredients of part 1 and mix intensively until a homogeneous gel is obtained.

EXAMPLE 33

| Hair Gel | |
|---|---|
| INCI Nomenclature | wt. % |
| Carbomer | 0.50 |
| Aqua (water) | Ad 100 |
| Triethanolamine | 0.70 |
| Condensation polymer according to the invention | 10.00 |
| Perfume oil | q.s. |
| PEG-40 Hydrogenated Castor Oil | q.s. |
| Methylparaben | 0.10 |
| Ethylhexyl Methoxycinnamate | 0.10 |
| PEG-14 Dimethicone | 0.10 |

Add all ingredients of part 1 and mix intensively until a homogeneous gel is obtained.

EXAMPLE 34

| Setting Lotion/Solution | |
|---|---|
| INCI Nomenclature | wt. % |
| Alcohol | Ad 100 |
| Aqua (water) | 30.00 |
| Dimethicone Copolyol | 0.10 |
| Perfume oil | 0.10 |
| Ethylhexyl Methoxycinnamate | 0.10 |
| Panthenol | 0.10 |
| Condensation polymer according to the invention | 7.00 |

Add all ingredients of part 1 and mix intensively until a homogeneous solution is obtained.

EXAMPLE 35

| Setting Lotion/Solution | |
|---|---|
| INCI Nomenclature | wt. % |
| Dimethicone Copolyol | 0.10 |
| Cylomethicone | 0.05 |
| Perfume oil | q.s. |
| Alcohol | Ad 100 |
| Aqua (water) | 40.00 |
| Condensation polymer according to the invention | 6.00 |

Add all ingredients of part 1 and mix intensively until a homogeneous solution is obtained.

EXAMPLE 36

| Setting Lotion/Solution | |
|---|---|
| INCI Nomenclature | wt. % |
| Panthenol | 0.10 |
| Nutrilan Keratin W | 0.10 |
| Hydrolyzed Elastin | 0.10 |
| Benzophenone-3 | 0.40 |
| Aqua (water) | 10.00 |
| Alcohol | Ad 100 |
| Perfume oil | q.s. |
| Condensation polymer according to the invention | 5.00 |

Add all ingredients and mix intensively until a homogeneous solution is obtained.

EXAMPLE 37

| Setting Lotion/Solution | |
|---|---|
| INCI Nomenclature | wt. % |
| Condensation polymer according to the invention | 4.00 |
| Polyquaternium-16 | 3.50 |
| Alcohol | Ad 100 |
| Aqua (water) | 20.00 |
| Perfume oil | q.s. |

Add all ingredients and mix intensively until a homogeneous solution is obtained.

EXAMPLE 38

| Setting Lotion/Solution | |
|---|---|
| INCI Nomenclature | wt. % |
| Condensation polymer according to the invention | 4.00 |
| PEG-8 | 0.20 |
| Perfume oil | 0.10 |
| Aqua (water) | 10.00 |
| Alcohol | 85.70 |

Add all ingredients and mix intensively until a homogeneous solution is obtained.

EXAMPLE 39

| Pump-Solution | |
|---|---|
| INCI Nomenclature | wt. % |
| Condensation polymer according to the invention | 26.00 |
| Alcohol | Ad 100 |
| Perfume oil | 0.10 |
| Ethylhexyl Methoxycinnamate | 0.10 |
| PEG/PPG-18/18 Dimethicone | 0.10 |

Add all ingredients and mix intensively until a homogeneous solution is obtained.

EXAMPLE 40

| Pump-Solution | |
|---|---|
| INCI Nomenclature | wt. % |
| Condensation polymer according to the invention | 26.00 |
| Polyvinyl caprolactam | 4.00 |
| Alcohol | Ad 100 |
| Ethylhexyl Methoxycinnamate | 0.10 |
| Cyclomethicone | 0.10 |
| Phenyl Trimethicone | 0.10 |

Add all ingredients and mix intensively until a homogeneous solution is obtained.

EXAMPLE 41

| Aerosol Spray NON VOC | |
|---|---|
| INCI Nomenclature | wt. % |
| Condensation polymer according to the invention | 13.00 |
| Perfume oil | 0.10 |
| Propylene Glycol | 0.10 |
| Triethyl Citrate | 0.10 |
| Aqua (water) | Ad 100 |
| Hydrofluorocarbon 152a | 40.00 |

Add all ingredients and mix intensively until a homogeneous solution is obtained.

EXAMPLE 42

| Aerosol Spray NON VOC | |
|---|---|
| INCI Nomenclature | wt. % |
| Condensation polymer according to the invention | 10.00 |
| VA/Crotonates/Vinyl Neodecanoate Copolymer | 2.00 |
| Aminomethyl Propanol | 0.16 |
| Perfume oil | 0.10 |
| Phytantriol | 0.10 |
| Aqua (water) | Ad 100 |
| Hydrofluorocarbon 152a | 35.00 |

Add all ingredients and mix intensively until a homogeneous solution is obtained.

EXAMPLE 43

| Aerosol Spray VOC 55 | |
|---|---|
| INCI Nomenclature | wt. % |
| Condensation polymer according to the invention | 7.00 |
| Polyurethane-1 Neodecanoate Copolymer | 7.00 |
| Alcohol | 14.30 |
| Aqua (water) | Ad 100 |
| Propylene Glycol | 0.10 |
| Perfume oil | 0.10 |
| Dimethylether | 40.00 |

Add all ingredients and mix intensively until a homogeneous solution is obtained.

EXAMPLE 44

| Aerosol Spray VOC 55 | |
|---|---|
| INCI Nomenclature | wt. % |
| Condensation polymer according to the invention | 10.00 |
| Polyvinylcaprolactam | 5.00 |
| Alcohol | 17.00 |
| Aqua (water) | Ad 100 |
| Niacinamide | 0.10 |
| Perfume oil | 0.10 |
| Dimethylether | 35.00 |

Add all ingredients and mix intensively until a homogeneous solution is obtained.

EXAMPLE 45

| Aerosol Spray VOC 80 | |
|---|---|
| INCI Nomenclature | wt. % |
| Condensation polymer according to the invention | 10.00 |
| Acrylates Copolymer | 1.00 |
| Aminomethyl Propanol | 0.24 |
| Alcohol | 35.00 |
| Aqua (water) | Ad 100 |
| Cyclopentylsiloxane | 0.10 |
| Perfume oil | 0.10 |
| Butane | 10.00 |
| Dimethylether | 35.00 |

Add all ingredients and mix intensively until a homogeneous solution is obtained.

EXAMPLE 46

| Aerosol Spray VOC 80 | |
|---|---|
| INCI Nomenclature | wt. % |
| Condensation polymer according to the invention | 10.00 |
| VP/VA Copolymer | 4.00 |
| Alcohol | Ad 100 |

Aerosol Spray VOC 80

| INCI Nomenclature | wt. % |
| --- | --- |
| Aqua (water) | 7.70 |
| Panthenol | 0.10 |
| Phenyl Trimethicone | 0.10 |
| Perfume oil | 0.10 |
| Dimethylether | 40.00 |

Add all ingredients and mix intensively until a homogeneous solution is obtained.

EXAMPLE 47

Waterfree Aerosol Spray

| INCI Nomenclature | wt. % |
| --- | --- |
| Condensation polymer according to the invention | 7.00 |
| PEG/PPG-25/25 Dimethicone/Acrylates Copolymer | 4.00 |
| Aminomethyl Propanol | 0.47 |
| Alcohol | Ad 100 |
| Diethyl Phthalate | 0.10 |
| Panthenol | 0.10 |
| Perfume oil | 0.10 |
| Propane/Butane | 10.00 |
| Dimethylether | 30 |

Add all ingredients and mix intensively until a homogeneous solution is obtained.

EXAMPLE 48

Waterfree Aerosol Spray

| INCI Nomenclature | wt. % |
| --- | --- |
| Condensation polymer according to the invention | 10.00 |
| Acrylates Copolymer | 1.00 |
| Aminomethyl Propanol | 0.17 |
| Alcohol | 43.53 |
| PEG-12 Dimethicone | 0.10 |
| Phenyl Trimethicone | 0.10 |
| Perfume oil | 0.10 |
| Dimethylether | Ad 100 |

Add all ingredients and mix intensively until a homogeneous solution is obtained.

EXAMPLE 49

Pump-Setting Mousse

| INCI Nomenclature | wt. % |
| --- | --- |
| Condensation polymer according to the invention | 3.00 |
| Hydroxyethyl Cetyldimonium Phosphate | 1.00 |
| Ceteareth-25 | 0.20 |
| Perfume oil | 0.40 |
| Aqua (water) | Ad 100 |
| Preservative | q.s. |

Add all ingredients and mix intensively until a homogeneous solution is obtained.

EXAMPLE 50

Pump-Spray

| | INCI Nomenclature | wt. % |
| --- | --- | --- |
| A | PEG-40 Hydrogenated Castor Oil | q.s. |
| | Perfume oil | q.s. |
| | Aqua (water) | Ad 100 |
| | Condensation polymer according to the invention | 7.30 |
| B | Propylen Glycol | 1.00 |
| | PEG-25 PABA | 0.20 |
| | Polyquaternium-16 | 1.00 |
| | Alcohol | 15.00 |

EXAMPLE 51

Styling Water

| | INCI Nomenclature | wt. % |
| --- | --- | --- |
| A | PEG-40 Hydrogenated Castor Oil | 0.70 |
| | Perfume oil | 0.20 |
| | Aqua (water) | Ad 100 |
| | Condensation polymer according to the invention | 7.30 |
| B | Propylen Glycol | 1.00 |
| | Polyquaternium-44 | 0.50 |
| | PEG-25 PABA | 0.20 |
| | Alcohol | 15.00 |

EXAMPLE 52

Hair Mousse

| | INCI Nomenclature | wt. % |
| --- | --- | --- |
| A | PEG-40 Hydrogenated Castor Oil | 0.70 |
| | Perfume oil | 0.20 |
| | Aqua (water) | Ad 100 |
| B | Cocotrimonium Methosulfate | 0.50 |
| | Condensation polymer according to the invention | 6.70 |
| | Polyquaternium-46 | 2.50 |
| | PEG-25 PABA | 0.20 |
| | PEG-8 | 0.50 |
| | Ceteareth-25 | 0.20 |
| | Preservative | q.s. |
| C | Propane/Butane | 10.00 |

EXAMPLE 53

Styling Mousse

| | INCI Nomenclature | wt. % |
| --- | --- | --- |
| A | Cocotrimonium Methosulfate | 2.00 |
| | Perfume oil | q.s. |

-continued

| | Styling Mousse | |
|---|---|---|
| | INCI Nomenclature | wt. % |
| B | Aqua (water) | Ad 100 |
| | Condensation polymer according to the invention | 7.00 |
| | Polyquaternuim-11 | 2.00 |
| | Ceteareth-25 | 0.20 |
| | Panthenol | 0.50 |
| | Benzophenone-4 | 0.05 |
| | Dow Corning 949 Cationic | 0.20 |
| | Alcohol | 15.00 |
| C | Hydroxyethylcellulose | 0.20 |
| D | Propane/Butane | 10.00 |

EXAMPLE 54

| | Setting Mousse | |
|---|---|---|
| | INCI Nomenclature | wt. % |
| A | Cocotrimonium Methosulfate | 2.00 |
| | Perfume oil | q.s. |
| B | Aqua (water) | Ad 100 |
| | Aminomethyl Propanol | 0.47 |
| | Preservative | 0.20 |
| | Dimethicone Copolyol | 0.20 |
| C | Condensation polymer according to the invention | 4.00 |
| D | Propane/Butane | 10.00 |

EXAMPLE 55

| | Wetlook Setting Mousse | |
|---|---|---|
| | INCI Nomenclature | wt. % |
| A | Cocotrimonium Methosulfate | 3.00 |
| | Perfume oil | 0.20 |
| B | Aqua (water) | Ad 100 |
| C | Glycerin | 5.00 |
| | Preservative | q.s. |
| | Condensation polymer according to the invention | 3.00 |
| D | Propane/Butane | 10.00 |

EXAMPLE 56

| Conditioning Mousse | |
|---|---|
| INCI Nomenclature | wt. % |
| Polyquaternium-11 | 5.00 |
| Condensation polymer according to the invention | 5.00 |
| Hydroxyethyl Cetyldimonium Phosphate | 0.50 |
| Alcohol | 10.00 |
| Perfume oil | 0.40 |
| Preservative | q.s. |
| Aqua (water) | Ad 100 |
| Propane/Butane | 10.00 |

EXAMPLE 57

| Gloss Hair Wax | |
|---|---|
| INCI Nomenclature | wt. % |
| Cetearyl Octanoate | 5.00 |
| Castor (*Ricinus Communis*) Oil | 5.00 |
| Petrolatum | 17.00 |
| Microcrystalline Wax | 7.00 |
| Beeswax | 6.00 |
| Condensation polymer according to the invention | 5.00 |
| 4-Methylbenzylidene | 3.00 |
| Butyl Methoxydibenzoylmethane | 2.00 |
| Phytantriol | 0.10 |
| Phenoxyethanol | 0.50 |
| Mineral Oil | Ad 100 |
| Phenyl Trimethicone | 11.00 |
| Perfume oil | q.s. |

EXAMPLE 58

| | Moisturizing Gel | |
|---|---|---|
| | INCI Nomenclature | wt. % |
| 1 | Hydroxyethylcellulose | 1.20 |
| | Aqua (water) | Ad 100 |
| 2 | Aqua (water) | 2.00 |
| | Sodium Metabisulfite | 0.10 |
| | Sodium Ascorbyl Phosphate | 0.50 |
| | Panthenol | 1.25 |
| 3 | Propylene Glycol | 5.00 |
| | Alcohol | 3.00 |
| | PEG/PPG-20/6 Dimethicone | 0.50 |
| 4 | Alcohol | 7.00 |
| | PEG-40 Hydrogenated Castor Oil | 0.80 |
| | Perfume oil | 0.40 |
| | Condensation polymer according to the invention | 2.00 |
| 5 | Citric Acid | 1.00 |

Dissolve Natrosol in Water. Add part 2 under slow agitation to part 1. Add part 3 under slow agitation. Mix all the ingredients of part 4 and add slowly under slow agitation. Adjust the pH 7.0 with part 5

EXAMPLE 59

| | Shower Oil | |
|---|---|---|
| | INCI Nomenclature | wt. % |
| 1 | MIPA-Laureth Sulfate & Laureth-4 & Cocamide DEA | Ad 100 |
| | Olive Oil PEG-7 Esters | 5.00 |
| | *Persea Gratissima* (Avocado) Oil | 35.65 |
| | Condensation polymer according to the invention | 2.00 |
| | Tocopherol | 0.10 |
| | Alcohol | 5.00 |
| | Bisabolol | 0.25 |
| | Panthenol | 2.00 |

Add all ingredients of part 1 and mix intensively until a homogeneous solution is obtained.

EXAMPLE 60

Anti Dandruff Shampoo

| INCI Nomenclature | wt. % |
|---|---|
| Aqua (water) | Ad 100 |
| Ammonium laureth sulphate | 10.00 |
| Ammonium lauryl sulphate | 5.00 |
| Glycol disearate | 1.00 |
| Dimethicone | 1.00 |
| Cetyl alcohol | 0.50 |
| Cocamide MEA | 3.00 |
| ZPT | 1.00 |
| Guar hydroxypropyltrimonium chloride | 0.20 |
| Hydrogenated polydecene | 1.00 |
| Polyquaternium 10 | 0.10 |
| PEG 7m | 0.50 |
| Trimethylpropane tricaprylate/tricaprate | 1.00 |
| Preservative | q.s. |
| Fragrance | 0.30 |
| E 104, E 110, E 132 | 0.02 |
| Condensation polymer according to the invention | 0.01-20 |

EXAMPLE 61

Conditioning Shampoo

| INCI Nomenclature | wt. % |
|---|---|
| Aqua (water) | Ad 100 |
| Sodium laureth sulphate | 8.00 |
| Cocamidopropyl betaine | 3.00 |
| Sodium chloride | 2.50 |
| Glycol distearate | 1.00 |
| Glycerin | 2.00 |
| Dimethiconol | 0.50 |
| Fragrance | 0.50 |
| Coco-glucoside | 3.00 |
| Carbomer | 0.10 |
| Arginine | 0.05 |
| Glyceryl oleate | 0.05 |
| Glyceryl stearate | 1.00 |
| Guar hydroxypropyltrimonium chloride | 0.10 |
| Panthenol | 1.00 |
| Disodium EDTA | 0.05 |
| Preservative | q.s. |
| Hydrolyzed keratin | 0.10 |
| Citric acid/sodium hydroxide | q.s |
| Condensation polymer according to the invention | 0.01-20 |
| E 102, E 110, FD&C blue | 0.01 |

EXAMPLE 62

Shampoo with plant extracts

| INCI Nomenclature | Wt. % |
|---|---|
| Aqua (water) | Ad 100 |
| Sodium laureth sulfate | 8.00 |
| Lauryl glucoside | 5.00 |
| Cocamidopropyl betaine, | 1.50 |
| Propylene glycol | 2.0 |
| Perfume oil | 1.25 |
| Sodium citrate | 0.25 |
| Sodium benzoate | 0.20 |

Shampoo with plant extracts (continued)

| INCI Nomenclature | Wt. % |
|---|---|
| Panthenol | 1.00 |
| Sodium formate | 0.20 |
| Polyquaternium-10 | 0.20 |
| Hydroxypropyl guar hydroxypropyltrimonium chloride | 0.05 |
| PEG-35 castor oil | 1.00 |
| Maris sal | 1.25 |
| Polysorbate 20 | 1.00 |
| Tocopheryl acetate | 0.20 |
| *Prunus armeniaca* | 0.20 |
| *Echinacea purpurea* | 0.05 |
| Retinyl palmitate | 0.05 |
| Tocopherol | 0.05 |
| Linoleic acid | 0.20 |
| Preservative | 1.00 |
| Condensation polymer according to the invention | 0.01-20 |
| CI77891 | 0.02 |

EXAMPLE 63

Shine Shampoo

| INCI Nomenclature | wt. % |
|---|---|
| Aqua (water) | Ad 100 |
| Sodium laureth sulfate | 5.00 |
| Disodium cocoamphodiacetate | 10.00 |
| Sodium chloride | 2.00 |
| Glycol distearate | 1.00 |
| Cocamidopropyl betaine | 2.00 |
| Laurdimonium hydroxypropyl hydrolyzed wheat protein | 1.00 |
| PEG-12 dimethicone | 1.00 |
| Guar hydroxypropyltrimonium chloride | 0.05 |
| Hydrolyzed wheat protein | 0.20 |
| Laureth-4 | 1.00 |
| PEG-7 glyceryl, cocoate | 2.00 |
| Hydrogenated castor oil | 1.00 |
| Laureth-2 | 0.50 |
| PEG-55 propylene glycol oleate | 2.00 |
| Propylene glycol | 2.00 |
| Mica | 0.20 |
| Citric acid | 0.01 |
| Fragrance | 1.00 |
| E 110, E 104, E 122 | 0.05 |
| Condensation polymer according to the invention | 0.01-20 |

The invention claimed is:

1. A hair care composition comprising a propellant and a branched condensation polymer, said condensation polymer being present in said composition within a concentration range of 0.01% to 20% by weight based on the total weight of the composition, said condensation polymer having at least one dialkylamide end-group connected to the polymer backbone through a unit derived from an alkylamide, the connection comprising at least one ester linkage, and wherein at least one nitrogen atom of the condensation polymer is present in a quaternized form or in a protonated form, and wherein the condensation polymer contains at least two end groups according to formula (I)

Formula I $$-\overset{O}{\underset{\|}{C}}-\underset{Y}{N}-\left[\overset{R^1}{\underset{R^2}{\overset{|}{C}}}\right]_n-\overset{R^3}{\underset{H}{\overset{|}{C}}}-O-\overset{O}{\underset{\|}{C}}-B-\overset{O}{\underset{\|}{C}}-\underset{R^8}{\overset{R^7}{\overset{|}{N}}}$$

wherein
Y is $$-\left[\overset{R^4}{\underset{R^5}{\overset{|}{C}}}\right]_n-\overset{R^6}{\underset{H}{\overset{|}{C}}}-O-\overset{O}{\underset{\|}{C}}-B-\overset{O}{\underset{\|}{C}}-\underset{R^8}{\overset{R^7}{\overset{|}{N}}},$$

a hydrogen atom, a linear, branched or cyclic ($C_1$-$C_{20}$) alkyl group or a ($C_6$-$C_{10}$) aryl group;
B is a ($C_6$-$C_{24}$) aryldiradical or a ($C_2$-$C_{24}$) alkyldiradical;
$R^1$, $R^2$, $R^3$, $R^4$, $R^5$ and $R^6$ are, independently of each other, hydrogen atoms, ($C_6$-$C_{10}$) aryl groups or ($C_1$-$C_8$) alkyl groups;
$R^7$ and $R^8$ are N,N-dimethylaminopropyl groups or $R^7$ and $R^8$ together with the nitrogen atom to which they are attached form a piperazine ring optionally substituted with at least one methyl group;
and n is an integer from 1 to 4, and
said hair care composition comprising at least one cosmetic or dermatological adjuvant or additive.

2. A hair care composition according to claim 1 wherein n is 1.

3. A hair care composition according to claim 1, characterized in that the condensation polymer has a number of dialkylamide endgroups equal to or greater than 3.

4. A hair care composition according to claim 1, characterized in that in the condensation polymer $R^3$ and $R^6$ are ($C_1$-$C_4$) alkyl groups.

5. A hair care composition according to claim 1, characterized in that the condensation polymer has a weight average molecular mass between 600 g/mol to 50,000 g/mol.

6. A hair care composition according to claim 1, characterized in that the condensation polymer has a number average molecular mass between 500 g/mol to 15,000 g/mol.

7. A hair care composition according to claim 1, characterized in that the average number of dialkylamide end-groups per condensation polymer is between 2 and 250.

8. A hair care composition according to claim 1, characterized in that the quaternized nitrogen are quaternized with linear, branched or cyclic ($C_1$-$C_8$) alkyl groups, unsaturated ($C_1$-$C_8$) alkyl groups, aryl groups, (meth-)acrylic groups or mixtures thereof or are in the form of a betaine group.

9. A hair care composition according to claim 8, characterized in that the quaternized nitrogen atoms of the condensation polymer are quaternized with methyl and/or ethyl groups.

10. A hair care composition according to claim 1 wherein the at least one cosmetic or dermatological adjuvant or additive is selected from the group consisting of a preservative, an antioxidant, a fatty substance, an oil, water, an organic solvent, a silicone, a thickener, a softener, an emulsifier, a screening agent, an antifoaming agent, a moisturizer, a fragrance, a surfactant, a filler, a sequestering agent, an anionic polymer, a cationic polymer, a nonionic polymer, an amphoteric polymer, an acidifying agent, a basifying agent, a light stabilizer, an insect repellent and an antibacterial agent.

11. The hair care composition of claim 1 in the form of a gel.

12. A method of treating hair in which a hair care composition of claim 1 is applied to the hair.

13. The hair care composition of claim 1 in the form of a spray.

14. A hair care composition comprising a propellant and a branched condensation polymer, said condensation polymer being present in said composition within a concentration range of 0.01% to 20% by weight based on the total weight of the composition, said condensation polymer having at least one dialkylamide end-group connected to the polymer backbone through a unit derived from an alkylamide, the connection comprising at least one ester linkage, and
wherein at least one nitrogen atom of the condensation polymer is present in a quaternized form or in a protonated form, and the condensation polymer is a polymer according to formula II Formula II $$A-\overset{O}{\underset{\|}{C}}-B-\overset{O}{\underset{\|}{C}}-\underset{Y}{N}-\overset{R^1}{\underset{R^2}{\overset{|}{C}}}-\overset{R^3}{\underset{H}{\overset{|}{C}}}-O-X^1$$

in which:
Y is $$-\overset{R^4}{\underset{R^5}{\overset{|}{C}}}-\overset{R^6}{\underset{H}{\overset{|}{C}}}-O-X^2,$$

a hydrogen atom, a ($C_1$-$C_{20}$) alkyl group or a ($C_6$-$C_{10}$) aryl group;
A is $$-\underset{Y}{N}-\overset{R^1}{\underset{R^2}{\overset{|}{C}}}-\overset{R^3}{\underset{H}{\overset{|}{C}}}-O-X^2 \text{ or OH};$$

B is a ($C_6$-$C_{24}$) aryl diradical or a ($C_2$-$C_{24}$) alkyl diradical;
$X^1$ is $$-\overset{O}{\underset{\|}{C}}-B-\overset{O}{\underset{\|}{C}}-\underset{Y}{N}-\overset{R^1}{\underset{R^2}{\overset{|}{C}}}-\overset{R^3}{\underset{H}{\overset{|}{C}}}-O-X^2;$$

$X^2$ is $$-\overset{O}{\underset{\|}{C}}-B-\overset{O}{\underset{\|}{C}}-\underset{R^8}{\overset{R^7}{\overset{|}{N}}},$$

a hydrogen atom or $X^1$;
$R^1$, $R^2$, $R^3$, $R^4$, $R^5$ and $R^6$ are, independently of each other, hydrogen atoms, ($C_6$-$C_{10}$) aryl groups or ($C_1$-$C_8$) alkyl groups or —$CH_2$—$OX^2$;
$R^7$ and $R^8$ are N,N-dimethylaminopropyl groups or $R^7$ and $R^8$ together with the nitrogen atom to which they are attached form a piperazine ring optionally substituted with at least one methyl group; and said hair care composition comprising at least one cosmetic or dermatological adjuvant or additive.

15. The hair care composition of claim 14 in the form of a gel.

16. The hair care composition of claim 14 in the form of a spray.

17. A method of treating hair in which a hair care composition of claim 14 is applied to the hair.

18. A hair care composition according to claim 14, wherein the quaternized nitrogen are quaternized with linear, branched or cyclic (C1-CS) alkyl groups, unsaturated (C1-CS) alkyl groups, aryl groups, (meth-)acrylic groups or mixtures thereof or are in the form of a betaine group.

19. A hair care composition according to claim 18, wherein the quaternized nitrogen atoms of the condensation polymer are quaternized with methyl and/or ethyl groups.

20. A hair care composition according to claim 14 wherein the at least one cosmetic or dermatological adjuvant or additive is selected from the group consisting of a preservative, an antioxidant, a fatty substance, an oil, water, an organic solvent, a silicone, a thickener, a softener, an emulsifier, a screening agent, an antifoaming agent, a moisturizer, a fragrance, a surfactant, a filler, a sequestering agent, an anionic polymer, a cationic polymer, a nonionic polymer, an amphoteric polymer, an acidifying agent, a basifying agent, a light stabilizer, an insect repellent and an antibacterial agent.

21. A hair care composition comprising a propellant and a branched condensation polymer, said condensation polymer being present in said composition within a concentration range of 0.01% to 20% by weight based on the total weight of the composition, said condensation polymer having at least one dialkylamide end-group connected to the polymer backbone through a unit derived from an alkylamide, the connection comprising at least one ester linkage, and wherein at least one nitrogen atom of the condensation polymer is present in a quaternized form or in a protonated form, and the condensation polymer is represented by formula (III):

Formula III

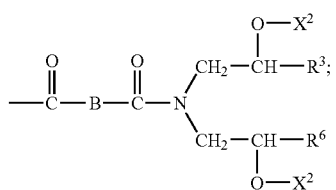

in which
A is

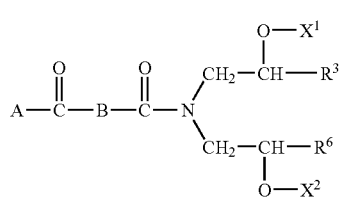

B is a $(C_6-C_{24})$ aryl diradical or a $(C_2-C_{24})$ alkyl diradical;

$X^1$ is

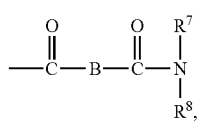

$X^2$ is

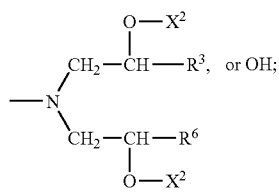

a hydrogen atom or $X^1$;

$R^3$ and $R^6$ are, independently of each other, hydrogen atoms, $(C_6-C_{10})$ aryl groups or $(C_1-C_8)$ alkyl groups or $-CH_2-OX^2$;

$R^7$ and $R^8$ are N,N-dimethylaminopropyl groups or $R^7$ and $R^8$ together with the nitrogen atom to which they are attached form a piperazine ring optionally substituted with at least one methyl group; and said hair care composition comprising at least one cosmetic or dermatological adjuvant or additive.

22. The hair care composition of claim 21 in the form of a gel.

23. The hair care composition of claim 21 in the form of a spray.

24. A method of treating hair in which a hair care composition of claim 21 is applied to the hair.

25. A hair care composition according to claim 21, wherein the quaternized nitrogen are quaternized with linear, branched or cyclic $(C_1-C_8)$ alkyl groups, unsaturated $(C_1-C_8)$ alkyl groups, aryl groups, (meth-)acrylic groups or mixtures thereof or are in the form of a betaine group.

26. A hair care composition according to claim 25, wherein the quaternized nitrogen atoms of the condensation polymer are quaternized with methyl and/or ethyl groups.

27. A hair care composition according to claim 21 wherein the at least one cosmetic or dermatological adjuvant or additive is selected from the group consisting of a preservative, an antioxidant, a fatty substance, an oil, water, an organic solvent, a silicone, a thickener, a softener, an emulsifier, a screening agent, an antifoaming agent, a moisturizer, a fragrance, a surfactant, a filler, a sequestering agent, an anionic polymer, a cationic polymer, a nonionic polymer, an amphoteric polymer, an acidifying agent, a basifying agent, a light stabilizer, an insect repellent and an antibacterial agent.

* * * * *